(12) United States Patent
Hampson et al.

(10) Patent No.: US 8,460,681 B2
(45) Date of Patent: Jun. 11, 2013

(54) SEQUENCES OF BRACHYSPIRA, IMMUNOGENIC COMPOUNDS, METHODS FOR PREPARATION AND USE THEREOF

(75) Inventors: David J. Hampson, Bedfordale (AU); Tom La, Parkwood (AU); Matthew I. Bellgard, Attadale (AU); Nyree D. Phillips, Kalamunda (AU)

(73) Assignee: Prionics AG, Schlieren (CH)

( * ) Notice: Subject to any disclaimer, the term of this patent is extended or adjusted under 35 U.S.C. 154(b) by 0 days.

(21) Appl. No.: 12/934,963

(22) PCT Filed: Mar. 26, 2009

(86) PCT No.: PCT/AU2009/000343
§ 371 (c)(1),
(2), (4) Date: Nov. 29, 2010

(87) PCT Pub. No.: WO2009/117773
PCT Pub. Date: Oct. 1, 2009

(65) Prior Publication Data
US 2011/0064756 A1      Mar. 17, 2011

(30) Foreign Application Priority Data

Mar. 27, 2008   (EP) ..................... 08153406

(51) Int. Cl.
*A61K 39/23*        (2006.01)
(52) U.S. Cl.
USPC ... 424/234.1; 435/7.1; 435/320.1; 435/252.3; 530/350; 536/23.7
(58) Field of Classification Search
None
See application file for complete search history.

(56) References Cited

U.S. PATENT DOCUMENTS

| 4,100,272 A * | 7/1978 | Glock et al. ............... 424/262.1 |
| 6,248,329 B1 * | 6/2001 | Chandrashekar et al. . 424/191.1 |
| 2008/0168583 A1 | 7/2008 | Fincher et al. |

FOREIGN PATENT DOCUMENTS

| WO | 03/095480 A2 | 11/2003 |
| WO | 2004/007726 A2 | 1/2004 |
| WO | 2006/119983 A2 | 11/2006 |
| WO | 2007/107323 A2 | 9/2007 |
| WO | 2008/017636 A2 | 2/2008 |
| WO | 2009/037279 A1 | 3/2009 |

OTHER PUBLICATIONS

The Dictionary of Immunology, Herbert et al eds, Academic Press, 1995, one page.*
Ellis, R.W. (Chapter 29 of "VACCINES" [Plotkin, S.A. et al. (eds) published by W. B. Saunders company (Philadelphia) in 1988.*
Feng et al (Infection and Immunity, 64(1):363-365, 1996).*
McGuinnes et al. (Mol. Microbiol. 7: 505-514, Feb. 1993).*
McGuinnes et al. (Lancet 337: 514-517, Mar. 1991).*
Houghten et al. (New Approaches to Immunization, Vaccines86, Cold Spring Harbor Laboratory, p. 21-25, 1986).*
Greenspan et al. (Nature Biotechnology 7: 936-937, 1999).*
Greenbaum et al, Journal of Molecular Recognition, 20(2):75-82, 2007.*
Blythe et al, Protein Science 14:246-248, 2005.*
Branden et al. (Introduction to Protein Structure, Garland Publishing Inc., New York, p. 247, 1991).*
Davis, A.J., et al., "The *Brachyspira hyodysenteriae* ftnA Gene: DNA Vaccination and Real-Time PCR Quantification of Bacteria in a Mouse Model of Disease," Current Microbiology 50(6):285-291, Jun. 2005.
Cullen, P.A., et al., "Characterization of a Locus Encoding Four Paralogous Outer Membrane Lipoproteins of *Brachyspira hyodysenteriae*," Microbes and Infection 5(4):275-283, Apr. 2003.
Gabe, J.D., et al., "Isolation of Extracytoplasmic Proteins from *Serpulina hyodysenteriae* B204 and Molecular Cloning of the flaB1 Gene Encoding a 38-Kilodalton Flagellar Protein," Infection and Immunity 63(1):142-148, Jan. 1995.
La, T., et al., "Protection of Pigs from Swine Dysentery by Vaccination With Recombinant BmpB, a 29.7 kDa Outer Membrane Lipoprotein of *Brachyspira hyodysenteriae*," Veterinary Microbiology 102(1-2):97-109, Aug. 2004.
International Search Report mailed Jun. 5, 2009, issued in corresponding PCT/AU2009/000343, filed Mar. 26, 2009, 5 pages.

* cited by examiner

*Primary Examiner* — Patricia A Duffy
(74) *Attorney, Agent, or Firm* — Christensen O'Connor Johnson Kindness PLLC

(57) ABSTRACT

Novel polynucleotide and amino acids of *Brachyspira hyodysenteriae* are described. These sequences are useful for diagnosis of *B. hyodysenteriae* disease in animals and as a therapeutic treatment or prophylactic treatment of *B. hyodysenteriae* disease in animals. These sequences may also be useful for diagnostic and therapeutic and/or prophylactic treatment of diseases in animals caused by other *Brachyspira* species.

10 Claims, No Drawings

SEQUENCE LISTING

<160> NUMBER OF SEQ ID NOS: 60

<210> SEQ ID NO 1
<211> LENGTH: 702
<212> TYPE: DNA
<213> ORGANISM: Brachyspira hyodysenteriae

<400> SEQUENCE: 1

| | | |
|---|---|---|
| atgaaaaaaa ttattatact tatcagctta tttactatgg tgtcggcatt agcctactct | 60 |
| catgctttag gtgtaggact ttatatccca ttaggcggaa gtattcctag cctatatcaa | 120 |
| acagacaatt taaatcctac tgcatcaata agtcctcaaa catcatttga agtaggtgtt | 180 |
| atatttaacc ctagagttac tttttaatgta aataaactta ataatgtatc tataggtata | 240 |
| gatgttggtt ggtatagaga tacatttaaa tttcaaactg attcaaaaaa ctttacacat | 300 |
| gaatttgata ctgttatgac aggtattaat ttcagatgga acctatgct atttgtatta | 360 |
| ggtataggag gaggcgttaa aattcctttc actggtaaat attgggaagg taataataac | 420 |
| atagcattaa gcgcaggtaa tttctcagct agatttaata atactgttat accttatgta | 480 |
| agactttata ctggtataga tttattcctt gtaagcttat ctttatatgt taattttgat | 540 |
| ataccatatt atcaaataaa agataattta gcttcattag gtgaaggata cagttatcct | 600 |
| ggaaaattag gatctgttga tataggtgtt cagctaggta ttcatttaga catatacaaa | 660 |
| ttcggagaag aagaagacga agaagaagaa agatatttat at | 702 |

<210> SEQ ID NO 2
<211> LENGTH: 234
<212> TYPE: PRT
<213> ORGANISM: Brachyspira hyodysenteriae

<400> SEQUENCE: 2

Met Lys Lys Ile Ile Ile Leu Ile Ser Leu Phe Thr Met Val Ser Ala
1               5                  10                  15

Leu Ala Tyr Ser His Ala Leu Gly Val Gly Leu Tyr Ile Pro Leu Gly
            20                  25                  30

Gly Ser Ile Pro Ser Leu Tyr Gln Thr Asp Asn Leu Asn Pro Thr Ala
        35                  40                  45

Ser Ile Ser Pro Gln Thr Ser Phe Glu Val Gly Val Ile Phe Asn Pro
    50                  55                  60

Arg Val Thr Phe Asn Val Asn Lys Leu Asn Asn Val Ser Ile Gly Ile
65                  70                  75                  80

Asp Val Gly Trp Tyr Arg Asp Thr Phe Lys Phe Gln Thr Asp Ser Lys
                85                  90                  95

Asn Phe Thr His Glu Phe Asp Thr Val Met Thr Gly Ile Asn Phe Arg
            100                 105                 110

Trp Asn Pro Met Leu Phe Val Leu Gly Ile Gly Gly Val Lys Ile
        115                 120                 125

Pro Phe Thr Gly Lys Tyr Trp Glu Gly Asn Asn Ile Ala Leu Ser
    130                 135                 140

Ala Gly Asn Phe Ser Ala Arg Phe Asn Asn Thr Val Ile Pro Tyr Val
145                 150                 155                 160

Arg Leu Tyr Thr Gly Ile Asp Leu Phe Leu Val Ser Leu Ser Leu Tyr
                165                 170                 175

Val Asn Phe Asp Ile Pro Tyr Tyr Gln Ile Lys Asp Asn Leu Ala Ser
            180                 185                 190

Leu Gly Glu Gly Tyr Ser Tyr Pro Gly Lys Leu Gly Ser Val Asp Ile
            195                 200                 205

Gly Val Gln Leu Gly Ile His Leu Asp Ile Tyr Lys Phe Gly Glu Glu
        210                 215                 220

Glu Asp Glu Glu Glu Glu Arg Tyr Leu Tyr
225                 230

<210> SEQ ID NO 3
<211> LENGTH: 942
<212> TYPE: DNA
<213> ORGANISM: Brachyspira hyodysenteriae

<400> SEQUENCE: 3
atgataatga ataaatcgca aaataaaaaa ctcgtaactt ttaaaatacc tgctacatct      60
gcgaatattg gttctgggtt tgatagtgta gggcttgctt tagatttgta taatgaaata     120
catatatatt ctaatgatga ttcaaaaaaa atagaatttg aaataagcgg agaaggtgaa     180
agcgagatat caaaagacaa taatatgata ctcgatgcta tgaaattagt atataaaga     240
ttaaagtcaa agcctgataa aggatatata ataaaatgta aaatagaat acctctttca     300
cgcggacttg gaagcagttc ggcagctata ataggaggac ttcttctgc taattatata      360
cttggaaaca aactatcaat tgaaaatgat atattgaata tgtctgttca gcttgaagga     420
caccctgaca atgtatctcc tgcaatattg ggaggtatta tatctggtgt agttcgtaaa     480
gatgaagatt ttaaatatgt gaaataaaaa ccacctaaag atttaaaagc tgtagttgca     540
attcctaact tttatttaag cactgaaact gcaagaaatg ctttgcctaa agaaataact     600
tttaaagatg ctatatttaa tatttcaagg gctgcacttc ttacttctgc attatcctca     660
aatagattag atttacttga ggttgctaca atgataaaac tgcatcagga ttacagagct     720
aagtttatac ctgggctaaa agatttattt aagaatacta aagcatcagg gcatattct     780
gttacaataa gcggtgcagg ttcttcaata cttctcttg taaaaacga tgaaaaggta     840
attaaaaaag tttctgaagc tatgaaaagc agtttcaata aaagaaaat agactgtgaa     900
ataaaagttt taaatatacc tcaaaaaggt gttataataa aa                       942

<210> SEQ ID NO 4
<211> LENGTH: 314
<212> TYPE: PRT
<213> ORGANISM: Brachyspira hyodysenteriae

<400> SEQUENCE: 4

Met Ile Met Asn Lys Ser Gln Asn Lys Lys Leu Val Thr Phe Lys Ile
1               5                   10                  15

Pro Ala Thr Ser Ala Asn Ile Gly Ser Gly Phe Asp Ser Val Gly Leu
            20                  25                  30

Ala Leu Asp Leu Tyr Asn Glu Ile His Ile Tyr Ser Asn Asp Asp Ser
        35                  40                  45

Lys Lys Ile Glu Phe Glu Ile Ser Gly Glu Gly Glu Ser Glu Ile Ser
    50                  55                  60

Lys Asp Asn Asn Met Ile Leu Asp Ala Met Lys Leu Val Tyr Lys Arg
65                  70                  75                  80

Leu Lys Ser Lys Pro Asp Lys Gly Tyr Ile Ile Lys Cys Ile Asn Arg
                85                  90                  95

Ile Pro Leu Ser Arg Gly Leu Gly Ser Ser Ala Ala Ile Ile Gly
            100                 105                 110

Gly Leu Leu Ser Ala Asn Tyr Ile Leu Gly Asn Lys Leu Ser Ile Glu
        115                 120                 125

Asn Asp Ile Leu Asn Met Ser Val Gln Leu Glu Gly His Pro Asp Asn
            130                 135                 140

Val Ser Pro Ala Ile Leu Gly Gly Ile Ile Ser Gly Val Val Arg Lys
145                 150                 155                 160

Asp Glu Asp Phe Lys Tyr Val Lys Ile Lys Pro Pro Lys Asp Leu Lys
                165                 170                 175

Ala Val Val Ala Ile Pro Asn Phe Tyr Leu Ser Thr Glu Thr Ala Arg
            180                 185                 190

Asn Ala Leu Pro Lys Glu Ile Thr Phe Lys Asp Ala Ile Phe Asn Ile
        195                 200                 205

Ser Arg Ala Ala Leu Leu Thr Ser Ala Leu Ser Ser Asn Arg Leu Asp
210                 215                 220

Leu Leu Glu Val Ala Thr Asp Asp Lys Leu His Gln Asp Tyr Arg Ala
225                 230                 235                 240

Lys Phe Ile Pro Gly Leu Lys Asp Leu Phe Lys Asn Thr Lys Ala Ser
                245                 250                 255

Gly Ala Tyr Ser Val Thr Ile Ser Gly Ala Gly Ser Ser Ile Leu Ser
            260                 265                 270

Leu Val Lys Asn Asp Glu Lys Val Ile Lys Val Ser Glu Ala Met
        275                 280                 285

Lys Ser Ser Phe Asn Lys Lys Lys Ile Asp Cys Glu Ile Lys Val Leu
290                 295                 300

Asn Ile Pro Gln Lys Gly Val Ile Ile Lys
305                 310

<210> SEQ ID NO 5
<211> LENGTH: 675
<212> TYPE: DNA
<213> ORGANISM: Brachyspira hyodysenteriae

<400> SEQUENCE: 5
atgaaaaaaa tatttatatt atttattttg ttttatcttt taatgctct ttattctgct        60 gactttgtta tgggctttgt aggaagagtt ggagccagca gtgctaccac tgatagaaat       120
aagatatttt catcagattt cagagatttt gataattctt tttcttttca gcctggaata       180
ttttggggat atgatgatct attatcaact gcatttcttt ttgatatagg atacagtaaa       240
gatagatacg aaatcaaata tactatagat ggaaaaagag tattagagaa ttatagtttt       300
ggaagttttt ctataggatt atttcctaga cttaatatag gattcttctc tataggtgta       360
ggtggaggaa ttaaattacc tatatcttta agtatacta tagagggagc tgaatttagc       420
agagaaagat attcattaga ttttggagat atacaagatg cctttacaac ttcatatatc       480
ccttatgtta agtttcagc agattttctt cttaaaatca gcaaaaaatt tatgatgtca       540
tttggtttat atgctaatta tgattttcct attaatatag ataaaaatgg tatattcaaa       600
gactttacaa tcaatcagga ttctttagct tcatttgata taggtttcca aatgggtatg       660
tatttcctaa gtaga                                                        675

<210> SEQ ID NO 6
<211> LENGTH: 225
<212> TYPE: PRT
<213> ORGANISM: Brachyspira hyodysenteriae

<400> SEQUENCE: 6

Met Lys Lys Ile Phe Ile Leu Phe Ile Leu Phe Leu Ser Phe Asn Ala
1               5                   10                  15

```
Leu Tyr Ser Ala Asp Phe Val Met Gly Phe Val Gly Arg Val Gly Ala
             20                  25                  30
Ser Ser Ala Thr Thr Asp Arg Asn Lys Ile Phe Ser Ser Asp Phe Arg
         35                  40                  45
Asp Phe Asp Asn Ser Phe Ser Phe Gln Pro Gly Ile Phe Trp Gly Tyr
 50                  55                  60
Asp Asp Leu Leu Ser Thr Ala Phe Leu Phe Asp Ile Gly Tyr Ser Lys
 65                  70                  75                  80
Asp Arg Tyr Glu Ile Lys Tyr Thr Ile Asp Gly Lys Arg Val Leu Glu
                 85                  90                  95
Asn Tyr Ser Phe Gly Ser Phe Ser Ile Gly Leu Phe Pro Arg Leu Asn
            100                 105                 110
Ile Gly Phe Phe Ser Ile Gly Val Gly Gly Ile Lys Leu Pro Ile
        115                 120                 125
Ser Leu Lys Tyr Thr Ile Glu Gly Ala Glu Phe Ser Arg Glu Arg Tyr
    130                 135                 140
Ser Leu Asp Phe Gly Asp Ile Gln Asp Ala Phe Thr Thr Ser Tyr Ile
145                 150                 155                 160
Pro Tyr Val Lys Val Ser Ala Asp Phe Leu Leu Lys Ile Ser Lys Lys
                165                 170                 175
Phe Met Met Ser Phe Gly Leu Tyr Ala Asn Tyr Asp Phe Pro Ile Asn
            180                 185                 190
Ile Asp Lys Asn Gly Ile Phe Lys Asp Phe Thr Ile Asn Gln Asp Ser
        195                 200                 205
Leu Ala Ser Phe Asp Ile Gly Phe Gln Met Gly Met Tyr Phe Leu Ser
    210                 215                 220
Arg
225

<210> SEQ ID NO 7
<211> LENGTH: 996
<212> TYPE: DNA
<213> ORGANISM: Brachyspira hyodysenteriae

<400> SEQUENCE: 7
atgaaaaaaa tatttttatt catttcaata atgtctttaa ttataattca atgcggtaat      60
aaaacagata ctcaaactac tgctgctaat acaaatgaag cagtacagtc aaataatact     120
ataccagcaa caaaaatatt atctcaagca gatacagcat ttttagagaa agtaaaaaat     180
aaaatagtaa tagacagaaa ttctcaatat actttcaaag agaatggaga tagaatat      240 gtatatgatt ctggagatta tagagaagat aaaaattata tatttgaatc ttcaaaagac     300
ggaactaatg cttattatta tgaaacttat aatatacaag atagatacaa agaaggacca     360
agcaatatag ctacaaatta tgaaggcttt tctgtaataa atggaattct ttatgaagat     420
aattatgaag gttatgaagg cgatcctatg gaaactataa tggttaaatg ggaaaaagaa     480
aattattatt ctaattacta ttacagagaa gtaaagaaa atcctaactt cgataatttc      540
ccttatgaga ataaagctga tgtaactttc gataactata tagaatatc aagaggtgtg      600 ttaatatcaa aatcagatta taaacttgaa gaagtagggg atattagcat gtataatttt     660
gataatgtat atacaaatgg ttataatgca tctattgaat aaagaaaaa tgatgacgga     720 acattctatt tctatgctat aatataact acagatgaaa acggacaaac agtaactaat     780
attcaaagca cagatgttag taaaatggta ttatcgaaaa atcagtatgt tgagccttat     840
tgtgaaatat ttgacgattc tattcagtat ggagaagttt acggtgctga tggtacatat     900
```

```
atgatagata taactcctat aagttctgat actttagttt tggttgaaaa ttatggaagc        960
tatggattca gcggagtttt taaaaagcag tctaat                                  996
```

<210> SEQ ID NO 8
<211> LENGTH: 332
<212> TYPE: PRT
<213> ORGANISM: Brachyspira hyodysenteriae

<400> SEQUENCE: 8

```
Met Lys Lys Ile Phe Leu Phe Ile Ser Ile Met Ser Leu Ile Ile Ile
1               5                   10                  15

Gln Cys Gly Asn Lys Thr Asp Thr Gln Thr Thr Ala Ala Asn Thr Asn
            20                  25                  30

Glu Ala Val Gln Ser Asn Asn Thr Ile Pro Ala Thr Lys Ile Leu Ser
        35                  40                  45

Gln Ala Asp Thr Ala Phe Leu Glu Lys Val Lys Asn Lys Ile Val Ile
    50                  55                  60

Asp Arg Asn Ser Gln Tyr Thr Phe Lys Glu Asn Gly Asp Ile Glu Tyr
65                  70                  75                  80

Val Tyr Asp Ser Gly Asp Tyr Arg Glu Asp Lys Asn Tyr Ile Phe Glu
                85                  90                  95

Ser Ser Lys Asp Gly Thr Asn Ala Tyr Tyr Glu Thr Tyr Asn Ile
            100                 105                 110

Gln Asp Arg Tyr Lys Glu Gly Pro Ser Asn Ile Ala Thr Asn Tyr Glu
        115                 120                 125

Gly Phe Ser Val Ile Asn Gly Ile Leu Tyr Glu Asp Asn Tyr Glu Gly
    130                 135                 140

Tyr Glu Gly Asp Pro Met Glu Thr Ile Met Val Lys Trp Glu Lys Glu
145                 150                 155                 160

Asn Tyr Tyr Ser Asn Tyr Tyr Arg Glu Val Lys Glu Asn Pro Asn
                165                 170                 175

Phe Asp Asn Phe Pro Tyr Glu Asn Lys Ala Asp Val Thr Phe Asp Asn
            180                 185                 190

Tyr Asn Arg Ile Ser Arg Gly Val Leu Ile Ser Lys Ser Asp Tyr Lys
        195                 200                 205

Leu Glu Glu Val Gly Asp Ile Ser Met Tyr Asn Phe Asp Asn Val Tyr
    210                 215                 220

Thr Asn Gly Tyr Asn Ala Ser Ile Glu Leu Lys Lys Asn Asp Asp Gly
225                 230                 235                 240

Thr Phe Tyr Phe Tyr Ala Ile Asn Ile Thr Thr Asp Glu Asn Gly Gln
                245                 250                 255

Thr Val Thr Asn Ile Gln Ser Thr Asp Val Ser Lys Met Val Leu Ser
            260                 265                 270

Glu Asn Gln Tyr Val Glu Pro Tyr Cys Glu Ile Phe Asp Asp Ser Ile
        275                 280                 285

Gln Tyr Gly Glu Val Tyr Gly Ala Asp Gly Thr Tyr Met Ile Asp Ile
    290                 295                 300

Thr Pro Ile Ser Ser Asp Thr Leu Val Leu Val Glu Asn Tyr Gly Ser
305                 310                 315                 320

Tyr Gly Phe Ser Gly Val Phe Lys Lys Gln Ser Asn
                325                 330
```

<210> SEQ ID NO 9
<211> LENGTH: 810
<212> TYPE: DNA
<213> ORGANISM: Brachyspira hyodysenteriae

<400> SEQUENCE: 9

```
atgttgaaaa ttaataagtt gaaaattgat aaagagaaaa ttatgaaaaa attattgaat      60
atatttataa taatgttttt aagctgtgtt actgttttttg caaaaagcgg tattgagata    120
ggtatatttg ttccattagg attaagtatt ggaataaatc aatatagttt aactaataaa    180
aatcctacac ctcagcaaga aaaagatttt gaatcggctg taaagcaggc agatagaaga    240
tcaggtgctg gatttgatgc gggtgttttg tttcatatag gatacagatt cgatataaat    300
agagatttta gcttcagtct tcttggagaa ttaggatata atcatgatga attttcattc    360
tatagagtga gcggagataa aaactataaa aatagttatg tttacatgtt tgaaagtatg    420
tcatttggaa tatatcccaa acttaattgg aagaaatttt cattcggatt gaattttgga    480
attaaagtgc ctttatacgc cagagctatg tcatcttata taaattatgc tgctaagaat    540
ataagcagga atatagaaaa ttataatgca tttcagataa agatatatt taatgtacct    600
attataccat atcttagatt ttctgtagat tatgaagttt acagtgataa aaaattcgga    660
ttagtattgg gaggttatat aggcggagat ttcggtatgt cttttaaaaa tactatatta    720
aataatcaaa gcatcgctaa aataacaaaa cagagtatat ctagttttga tataggtttc    780
caaataggtg ttagaatact tcctaataat                                     810
```

<210> SEQ ID NO 10
<211> LENGTH: 270
<212> TYPE: PRT
<213> ORGANISM: Brachyspira hyodysenteriae

<400> SEQUENCE: 10

```
Met Leu Lys Ile Asn Lys Leu Lys Ile Asp Lys Glu Lys Ile Met Lys
  1               5                  10                  15

Lys Leu Leu Asn Ile Phe Ile Ile Met Phe Leu Ser Cys Val Thr Val
             20                  25                  30

Phe Ala Lys Ser Gly Ile Glu Ile Gly Ile Phe Val Pro Leu Gly Leu
         35                  40                  45

Ser Ile Gly Ile Asn Gln Tyr Ser Leu Thr Asn Lys Asn Pro Thr Pro
     50                  55                  60

Gln Gln Glu Lys Asp Phe Glu Ser Ala Val Lys Gln Ala Asp Arg Arg
 65                  70                  75                  80

Ser Gly Ala Gly Phe Asp Ala Gly Val Leu Phe His Ile Gly Tyr Arg
                 85                  90                  95

Phe Asp Ile Asn Arg Asp Phe Ser Phe Ser Leu Leu Gly Glu Leu Gly
            100                 105                 110

Tyr Asn His Asp Glu Phe Ser Phe Tyr Arg Val Ser Gly Asp Lys Asn
        115                 120                 125

Tyr Lys Asn Ser Tyr Val Tyr Met Phe Glu Ser Met Ser Phe Gly Ile
    130                 135                 140

Tyr Pro Lys Leu Asn Trp Lys Lys Phe Ser Phe Gly Leu Asn Phe Gly
145                 150                 155                 160

Ile Lys Val Pro Leu Tyr Ala Arg Ala Met Ser Ser Tyr Ile Asn Tyr
                165                 170                 175

Ala Ala Lys Asn Ile Ser Arg Asn Ile Glu Asn Tyr Asn Ala Phe Gln
            180                 185                 190

Ile Lys Asp Ile Phe Asn Val Pro Ile Ile Pro Tyr Leu Arg Phe Ser
        195                 200                 205

Val Asp Tyr Glu Val Tyr Ser Asp Lys Lys Phe Gly Leu Val Leu Gly
    210                 215                 220
```

Gly Tyr Ile Gly Gly Asp Phe Gly Met Ser Phe Lys Asn Thr Ile Leu
225                 230                 235                 240

Asn Asn Gln Ser Ile Ala Lys Ile Thr Lys Gln Ser Ile Ser Ser Phe
            245                 250                 255

Asp Ile Gly Phe Gln Ile Gly Val Arg Ile Leu Pro Asn Asn
        260                 265                 270

<210> SEQ ID NO 11
<211> LENGTH: 639
<212> TYPE: DNA
<213> ORGANISM: Brachyspira hyodysenteriae

<400> SEQUENCE: 11
atgaagaaaa tttttactat aacagcaatg ttaataataa ctataagtgc aaatcttatg       60
gctaaaagcg gattcggagt tgatttaact gtaccttttgg gagcaggtat tggttttatt      120
tatgaagacg gtaaagaaag taaaacttat aaacctgacg gagggtttga attcggtgta      180
tatttaagac ctaattatta ttttgattta agtgtattat ctttgggaat agcattagat      240
tttggatatc aaagagatgt atttgcctat aaatcagata ttagtaaagg taacttaaca      300
tttgatagtt tgggtgttgg attaatgcct aaaattgata tattattttt gtctataggt      360
gttggagcag gtgtaaaatt ccctctcgga ggaagcagtt attccaaaga aaatagcggc      420
ggagaacaaa ggaattcata ctcttttaaaa gatttacaaa atcaatataa taatttatat      480
ataccatacc ttaaagcaac tttagatttt cttttattat ataatttcac tttaggtatt      540
tatatgtctt atgatttccc tgttatggaa tataaagaag tttctccaaa aataacattt      600
ggaggatttg atataggcgg tcaaataggt ataagattc                              639

<210> SEQ ID NO 12
<211> LENGTH: 213
<212> TYPE: PRT
<213> ORGANISM: Brachyspira hyodysenteriae

<400> SEQUENCE: 12

Met Lys Lys Ile Leu Leu Ile Thr Ala Met Leu Ile Ile Thr Ile Ser
1               5                   10                  15

Ala Asn Leu Met Ala Lys Ser Gly Phe Gly Val Asp Leu Thr Val Pro
            20                  25                  30

Leu Gly Ala Gly Ile Gly Phe Ile Tyr Glu Asp Gly Lys Glu Ser Lys
        35                  40                  45

Thr Tyr Lys Pro Asp Gly Gly Phe Glu Phe Gly Val Tyr Leu Arg Pro
    50                  55                  60

Asn Tyr Tyr Phe Asp Leu Ser Val Leu Ser Leu Gly Ile Ala Leu Asp
65                  70                  75                  80

Phe Gly Tyr Gln Arg Asp Val Phe Ala Tyr Lys Ser Asp Ile Ser Lys
                85                  90                  95

Gly Asn Leu Thr Phe Asp Ser Leu Gly Val Gly Leu Met Pro Lys Ile
            100                 105                 110

Asp Ile Leu Phe Leu Ser Ile Gly Val Gly Ala Gly Val Lys Phe Pro
        115                 120                 125

Leu Gly Gly Ser Ser Tyr Ser Lys Glu Asn Ser Gly Gly Glu Gln Arg
    130                 135                 140

Asn Ser Tyr Ser Leu Lys Asp Leu Gln Asn Gln Tyr Asn Asn Leu Tyr
145                 150                 155                 160

Ile Pro Tyr Leu Lys Ala Thr Leu Asp Phe Leu Leu Leu Tyr Asn Phe
                165                 170                 175

Thr Leu Gly Ile Tyr Met Ser Tyr Asp Phe Pro Val Met Glu Tyr Lys
            180                 185                 190

Glu Val Ser Pro Lys Ile Thr Phe Gly Gly Phe Asp Ile Gly Gly Gln
        195                 200                 205

Ile Gly Ile Arg Phe
    210

<210> SEQ ID NO 13
<211> LENGTH: 1239
<212> TYPE: DNA
<213> ORGANISM: Brachyspira hyodysenteriae

<400> SEQUENCE: 13

```
atgaaattta tattgaataa gttatatcta tttatatttt tatctttatt ttttatatca    60
tgtgctacaa cttctaaaag tacatcaagc ggcggagtat atgtaggaga agataccgga   120
gaaataggaa tagttaataa ttggaagaat cctgatttca aaggcggaaa aactacaaaa   180
ataatcgctg aaggttatgc atctgctgat ggaagaggtg aggctgatgc tatagaaaga   240
tccattgaaa gtgctaaaag aaatgcagta gagcaggcag ttggttctat agttaatgga   300
agtactttag ttgaaaataa tagacttata agttctaaaa tatatgacaa tacaacaggt   360
tatatatctt catataaagt aattaatata tccaaatccg gttctgtttg gtattctaag   420
atagaggcta cagttggcgt tgatatgctt caagataatc ttcaggcaat gggcatactg   480
atggacagaa aaaatcttcc tcttatagtt gtgcttgtta cagatgaaac aggaaattta   540
agcgaatctt ttaacgtgga attagaaaaa aatatgagtg agaaaggatt taaatttgtt   600
agtccttcat cacttcaaaa tgttatgaga aagaaaata taagttatga agatacaaga   660
ggttctcgtt cgtcagcttc aataaaaaag atagctgatg ctacaggggc acaaatagct   720
ataataggta agcagatgc tgctttcttt acaactatac aaggcactgc tatgaaaagt   780
tatagaagcg atgttgcaat aactgctatt aatatatctg attatactac catagcaaga   840
gctacacatc aggcaggcgg tgtaggagga agcgataagg atgcacattc catagctttg   900
gttaaatcag cagattatgt atcagatgat tttgttaatc agatagttaa taatggcag   960
agtgaagttc aaaacggtac agagtatact atatatgtaa gcggacttga ttttaatgaa  1020
tctataggtt ttgaagaggc tttgaaaaag aatataggcg gattaaaaaa tatttataat  1080
agaggagtat ctggagagtc ttctaggtat gttgttactt atgtaggaag cagcagagat  1140
ttagcagttg atattaattc taaagctaaa agtatgggat atcaagtaat aataagtagt  1200
tttgatgata aaactattac tttaaaggca agtaagagg                         1239
```

<210> SEQ ID NO 14
<211> LENGTH: 413
<212> TYPE: PRT
<213> ORGANISM: Brachyspira hyodysenteriae

<400> SEQUENCE: 14

Met Lys Phe Ile Leu Asn Lys Leu Tyr Leu Phe Ile Phe Leu Ser Leu
1               5                   10                  15

Phe Phe Ile Ser Cys Ala Thr Thr Ser Lys Ser Thr Ser Ser Gly Gly
            20                  25                  30

Val Tyr Val Gly Glu Asp Thr Gly Glu Ile Gly Ile Val Asn Asn Trp
        35                  40                  45

Lys Asn Pro Asp Phe Lys Gly Gly Lys Thr Thr Lys Ile Ile Ala Glu
    50                  55                  60

```
Gly Tyr Ala Ser Ala Asp Gly Arg Gly Glu Ala Asp Ala Ile Glu Arg
 65                  70                  75                  80

Ser Ile Glu Ser Ala Lys Arg Asn Ala Val Glu Gln Ala Val Gly Ser
                 85                  90                  95

Ile Val Asn Gly Ser Thr Leu Val Glu Asn Asn Arg Leu Ile Ser Ser
            100                 105                 110

Lys Ile Tyr Asp Asn Thr Thr Gly Tyr Ile Ser Ser Tyr Lys Val Ile
        115                 120                 125

Asn Ile Ser Lys Ser Gly Ser Val Trp Tyr Ser Lys Ile Glu Ala Thr
    130                 135                 140

Val Gly Val Asp Met Leu Gln Asp Asn Leu Gln Ala Met Gly Ile Leu
145                 150                 155                 160

Met Asp Arg Lys Asn Leu Pro Leu Ile Val Leu Val Thr Asp Glu
                165                 170                 175

Thr Gly Asn Leu Ser Glu Ser Phe Asn Val Glu Leu Glu Lys Asn Met
                180                 185                 190

Ser Glu Lys Gly Phe Lys Phe Val Ser Pro Ser Ser Leu Gln Asn Val
            195                 200                 205

Met Arg Lys Glu Asn Ile Ser Tyr Glu Asp Thr Arg Gly Ser Arg Ser
    210                 215                 220

Ser Ala Ser Ile Lys Lys Ile Ala Asp Ala Thr Gly Ala Gln Ile Ala
225                 230                 235                 240

Ile Ile Gly Lys Ala Asp Ala Phe Phe Thr Thr Ile Gln Gly Thr
                245                 250                 255

Ala Met Lys Ser Tyr Arg Ser Asp Val Ala Ile Thr Ala Ile Asn Ile
                260                 265                 270

Ser Asp Tyr Thr Thr Ile Ala Arg Ala Thr His Gln Ala Gly Val
            275                 280                 285

Gly Gly Ser Asp Lys Asp Ala His Ser Ile Ala Leu Val Lys Ser Ala
        290                 295                 300

Asp Tyr Val Ser Asp Asp Phe Val Asn Gln Ile Val Asn Lys Trp Gln
305                 310                 315                 320

Ser Glu Val Gln Asn Gly Thr Glu Tyr Thr Ile Tyr Val Ser Gly Leu
                325                 330                 335

Asp Phe Asn Glu Ser Ile Gly Phe Glu Glu Ala Leu Lys Lys Asn Ile
            340                 345                 350

Gly Gly Leu Lys Asn Ile Tyr Asn Arg Gly Val Ser Gly Glu Ser Ser
        355                 360                 365

Arg Tyr Val Val Thr Tyr Val Gly Ser Ser Arg Asp Leu Ala Val Asp
    370                 375                 380

Ile Asn Ser Lys Ala Lys Ser Met Gly Tyr Gln Val Ile Ile Ser Ser
385                 390                 395                 400

Phe Asp Asp Lys Thr Ile Thr Leu Lys Ala Ser Lys Arg
                405                 410

<210> SEQ ID NO 15
<211> LENGTH: 759
<212> TYPE: DNA
<213> ORGANISM: Brachyspira hyodysenteriae

<400> SEQUENCE: 15
atgaaaaaaa tattcattac aatattttca tttctattat tttttgcaaa tacattattc      60
tcacaatttg atgctagcat atatgcacca ttatctttta cattaacatt tcctatgttg     120
gatactaaaa atgttaatgt aaataatctt aaaggaaatg aagtttttc tgcaggagtt     180
```

```
ataggaaatt tcggacataa attttcaata aatgatggta aatattctat aagtgtttta    240
acagagattg gatattacag acaaactttt tcagcatcat ttcattattc ttccatagag    300
tttaaagata ctttagcttt tgataccttta ttagttggtg taatgcctaa attcaatata    360
gatttaaaag atttgcttac atctataagt cctaattata atattaaaac agtattaagt    420
ataggtattg gttttggaat gaaaatacct tttggaggat atgcagagag ttatattgac    480
ggtacaggag aaaatcaaaa actttctttc aatgatataa ataaaaattt tacttatcct    540
attataccat atataaaatt gcaattagat gattattttt attttaatga acatgttgca    600
tttttatttg gatttaatat aacttatgac tttggtatat tttatgatat tgattatatt    660
gacagtcagt taggagctcc gttattaagc agttttataa ataagtatgg atttagcagt    720
ttagaaattg ctttaaattt tggaataaaa tttggaaat                           759
```

<210> SEQ ID NO 16
<211> LENGTH: 253
<212> TYPE: PRT
<213> ORGANISM: Brachyspira hyodysenteriae
<400> SEQUENCE: 16

```
Met Lys Lys Ile Phe Ile Thr Ile Phe Ser Phe Leu Leu Phe Phe Ala
1               5                  10                  15

Asn Thr Leu Phe Ser Gln Phe Asp Ala Ser Ile Tyr Ala Pro Leu Ser
            20                  25                  30

Phe Thr Leu Thr Phe Pro Met Leu Asp Thr Lys Asn Val Asn Val Asn
        35                  40                  45

Asn Leu Lys Gly Asn Gly Ser Phe Ser Ala Gly Val Ile Gly Asn Phe
    50                  55                  60

Gly His Lys Phe Ser Ile Asn Asp Gly Lys Tyr Ser Ile Ser Val Leu
65                  70                  75                  80

Thr Glu Ile Gly Tyr Tyr Arg Gln Thr Phe Ser Ala Ser Phe His Tyr
                85                  90                  95

Ser Ser Ile Glu Phe Lys Asp Thr Leu Ala Phe Asp Thr Leu Leu Val
            100                 105                 110

Gly Val Met Pro Lys Phe Asn Ile Asp Leu Lys Asp Leu Leu Thr Ser
        115                 120                 125

Ile Ser Pro Asn Tyr Asn Ile Lys Thr Val Leu Ser Ile Gly Ile Gly
    130                 135                 140

Phe Gly Met Lys Ile Pro Phe Gly Gly Tyr Ala Glu Ser Tyr Ile Asp
145                 150                 155                 160

Gly Thr Gly Glu Asn Gln Lys Leu Ser Phe Asn Asp Ile Asn Lys Asn
                165                 170                 175

Phe Thr Tyr Pro Ile Ile Pro Tyr Ile Lys Leu Gln Leu Asp Asp Tyr
            180                 185                 190

Phe Tyr Phe Asn Glu His Val Ala Phe Leu Gly Phe Asn Ile Thr
        195                 200                 205

Tyr Asp Phe Gly Ile Phe Tyr Asp Ile Asp Tyr Ile Asp Ser Gln Leu
    210                 215                 220

Gly Ala Pro Leu Leu Ser Ser Phe Ile Asn Lys Tyr Gly Phe Ser Ser
225                 230                 235                 240

Leu Glu Ile Ala Leu Asn Phe Gly Ile Lys Phe Gly Asn
                245                 250
```

<210> SEQ ID NO 17
<211> LENGTH: 792
<212> TYPE: DNA

<213> ORGANISM: Brachyspira hyodysenteriae

<400> SEQUENCE: 17

```
atggcttttg attttaaact gatagtaaga gataaatatt cagaagagat tttgatattt    60
ataaatacag ttcaaagcat aaaggctgat gatataaaaa ctgattataa agtaactgac   120
ggaagcagat catactctat aaaaacaggc ataggaaata ttgcaagcgg aagaactttt   180
aatataggta ttcctattta tgaatataaa aatgaattag gttcttgggt aagaatagaa   240
gaacaatata ctaaatatac aagcatggtt ttatcaagca atattaaaag atatttcata   300
agaactatat ttgaagatga agtttatgaa gcagaatata tcatgaaatc agttggcgga   360
tataatataa aatatataaa taatttgggt gtgatagata tttcacttga agcattggac   420
aaagtttttc taagacaaaa agaagaggaa tatgaactgc ctattacaga agaaaataaa   480
caggatataa attataaatc attaagttta gttcctgtgc ctgtaaattt taatttggag   540
tttatagttg taggcggagc attggagttc ttatttgcta atagacagaa ctttggaata   600
cagtttaatg cagagctaag aaatggagtt tataatattg attttgacgg tgagaaatta   660
aatgtaaatg gagtagctta taattataaa ggagttcagc ctgaattaaa tgttggtaat   720
aatgtatttt atttagaaag taatcaaact tgtgttaagg cttctataag ctataaaaga   780
ggaatattaa ta                                                         792
```

<210> SEQ ID NO 18
<211> LENGTH: 264
<212> TYPE: PRT
<213> ORGANISM: Brachyspira hyodysenteriae

<400> SEQUENCE: 18

```
Met Ala Phe Asp Phe Lys Leu Ile Val Arg Asp Lys Tyr Ser Glu Glu
1               5                   10                  15

Ile Phe Asp Ile Ile Asn Thr Val Gln Ser Ile Lys Ala Asp Asp Ile
            20                  25                  30

Lys Thr Asp Tyr Lys Val Thr Asp Gly Ser Arg Ser Tyr Ser Ile Lys
        35                  40                  45

Thr Gly Ile Gly Asn Ile Ala Ser Gly Arg Thr Phe Asn Ile Gly Ile
    50                  55                  60

Pro Ile Tyr Glu Tyr Lys Asn Glu Leu Gly Ser Trp Val Arg Ile Glu
65                  70                  75                  80

Glu Gln Tyr Thr Lys Tyr Thr Ser Met Val Leu Ser Ser Asn Ile Lys
                85                  90                  95

Arg Tyr Phe Ile Arg Thr Ile Phe Glu Asp Glu Val Tyr Glu Ala Glu
            100                 105                 110

Tyr Ile Met Lys Ser Val Gly Gly Tyr Asn Ile Lys Tyr Ile Asn Asn
        115                 120                 125

Leu Gly Val Ile Asp Ile Ser Leu Glu Ala Leu Asp Lys Val Phe Leu
    130                 135                 140

Arg Gln Lys Glu Glu Glu Tyr Glu Leu Pro Ile Thr Glu Glu Asn Lys
145                 150                 155                 160

Gln Asp Ile Asn Tyr Lys Ser Leu Ser Leu Val Pro Val Pro Val Asn
                165                 170                 175

Phe Asn Leu Glu Phe Ile Val Val Gly Gly Ala Leu Glu Phe Leu Phe
            180                 185                 190

Ala Asn Arg Gln Asn Phe Gly Ile Gln Phe Asn Ala Glu Leu Arg Asn
        195                 200                 205

Gly Val Tyr Asn Ile Asp Phe Asp Gly Glu Lys Leu Asn Val Asn Gly
```

```
                210                 215                 220
Val Ala Tyr Asn Tyr Lys Gly Val Gln Pro Glu Leu Asn Val Gly Asn
225                 230                 235                 240

Asn Val Phe Tyr Leu Glu Ser Asn Gln Thr Cys Val Lys Ala Ser Ile
            245                 250                 255

Ser Tyr Lys Arg Gly Ile Leu Ile
        260
```

<210> SEQ ID NO 19
<211> LENGTH: 639
<212> TYPE: DNA
<213> ORGANISM: Brachypira hyodysenteriae

<400> SEQUENCE: 19

```
atgaaaaaaa taataacaat ctcatgctta ttaatcattg cattaagcgg aaatttgatg    60
gcaaaaacag gatttgaggt taatgtatta tttcctttcg gtttaagttt aggaacatat   120
actggaacgg atgcgtctaa atatactaaa gctgatgctg gttttgaatt tggtattcat   180
gttatacctg gatattattt cggaataagt aatatagctt taggaatagg tcttgatata   240
ggttatcaaa aagatgtatt tgctttcgga ttaaaaggag aaaaaggaag atacggagct   300
tcttttgata gttttaatct tggtttgctt cctagaatag atttggcttt catatcaata   360
ggtgtaggcg gaggatttaa attccctata gcaggactta tgtatagtaa agaaagcagc   420
gacagcatag gtcaagctag catgtatgat acaaaaacaa tatataaaga attcaataag   480 cctttatac cttatgtaaa agttacactc gatttcattt tacctcttaa tttaactgct   540
ggtatttatg ttgcttatga tattccattt atggaaagta aaactcatga ctttaaatta   600
tcaagtgttg atttaggtgc tcagattgga ataagattt                          639
```

<210> SEQ ID NO 20
<211> LENGTH: 213
<212> TYPE: PRT
<213> ORGANISM: Brachyspira hyodysenteriae

<400> SEQUENCE: 20

```
Met Lys Lys Ile Ile Thr Ile Ser Cys Leu Leu Ile Ile Ala Leu Ser
1               5                   10                  15

Gly Asn Leu Met Ala Lys Thr Gly Phe Glu Val Asn Val Leu Phe Pro
            20                  25                  30

Phe Gly Leu Ser Leu Gly Thr Tyr Thr Gly Thr Asp Ala Ser Lys Tyr
        35                  40                  45

Thr Lys Ala Asp Ala Gly Phe Glu Phe Gly Ile His Val Ile Pro Gly
50                  55                  60

Tyr Tyr Phe Gly Ile Ser Asn Ile Ala Leu Gly Ile Gly Leu Asp Ile
65                  70                  75                  80

Gly Tyr Gln Lys Asp Val Phe Ala Phe Gly Leu Lys Gly Glu Lys Gly
                85                  90                  95

Arg Tyr Gly Ala Ser Phe Asp Ser Phe Asn Leu Gly Leu Leu Pro Arg
            100                 105                 110

Ile Asp Leu Ala Phe Ile Ser Ile Gly Val Gly Gly Phe Lys Phe
        115                 120                 125

Pro Ile Ala Gly Leu Met Tyr Ser Lys Glu Ser Asp Ser Ile Gly
    130                 135                 140

Gln Ala Ser Met Tyr Asp Thr Lys Thr Ile Tyr Lys Glu Phe Asn Lys
145                 150                 155                 160

Pro Phe Ile Pro Tyr Val Lys Val Thr Leu Asp Phe Ile Leu Pro Leu
```

```
                165                 170                 175
Asn Leu Thr Ala Gly Ile Tyr Val Ala Tyr Asp Ile Pro Phe Met Glu
            180                 185                 190

Ser Lys Thr His Asp Phe Lys Leu Ser Ser Val Asp Leu Gly Ala Gln
        195                 200                 205

Ile Gly Ile Arg Phe
    210
```

<210> SEQ ID NO 21
<211> LENGTH: 27
<212> TYPE: DNA
<213> ORGANISM: Artificial
<220> FEATURE:
<223> OTHER INFORMATION: Primer

<400> SEQUENCE: 21
gcttatttac tatggtgtcg gcattag                                        27

<210> SEQ ID NO 22
<211> LENGTH: 27
<212> TYPE: DNA
<213> ORGANISM: Artificial
<220> FEATURE:
<223> OTHER INFORMATION: Primer

<400> SEQUENCE: 22
atatctttct tcttcttcgt cttcttc                                        27

<210> SEQ ID NO 23
<211> LENGTH: 27
<212> TYPE: DNA
<213> ORGANISM: Artificial
<220> FEATURE:
<223> OTHER INFORMATION: Primer

<400> SEQUENCE: 23
agaatacctc tttcacgcgg acttgga                                        27

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
acctcccaat attgcaggag                                                20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
tttgttatgg gctttgtagg                                                20

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
aagaagaaaa tctgctgaaa c                                              21

<210> SEQ ID NO 27
<211> LENGTH: 26
<212> TYPE: DNA
<213> ORGANISM: Artificial
<220> FEATURE:
<223> OTHER INFORMATION: Primer

<400> SEQUENCE: 27
attcaatgcg gtaataaaac agatac                                         26

<210> SEQ ID NO 28
<211> LENGTH: 26
<212> TYPE: DNA
<213> ORGANISM: Artificial
<220> FEATURE:
<223> OTHER INFORMATION: Primer

<400> SEQUENCE: 28
atgctaatat cccctacttc ttcaag                                         26

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
tgaatcggct gtaaagcagg ca                                             22

<210> SEQ ID NO 30
<211> LENGTH: 26
<212> TYPE: DNA
<213> ORGANISM: Artificial
<220> FEATURE:
<223> OTHER INFORMATION: Primer

<400> SEQUENCE: 30
acacccgcat caaatccagc acctga                                         26

<210> SEQ ID NO 31
<211> LENGTH: 25
<212> TYPE: DNA
<213> ORGANISM: Artificial
<220> FEATURE:
<223> OTHER INFORMATION: Primer

<400> SEQUENCE: 31
tcttatggct aaaagcggat tcgga                                          25

<210> SEQ ID NO 32
<211> LENGTH: 28
<212> TYPE: DNA
<213> ORGANISM: Artificial
<220> FEATURE:
<223> OTHER INFORMATION: Primer

<400> SEQUENCE: 32
gagggaattt tacacctgct ccaacacc                                       28

<210> SEQ ID NO 33
<211> LENGTH: 22
<212> TYPE: DNA
<213> ORGANISM: Artificial

```
<220> FEATURE:
<223> OTHER INFORMATION: Primer

<400> SEQUENCE: 33
tcgctgaagg ttatgcatct gc                                    22

<210> SEQ ID NO 34
<211> LENGTH: 28
<212> TYPE: DNA
<213> ORGANISM: Artificial
<220> FEATURE:
<223> OTHER INFORMATION: Primer

<400> SEQUENCE: 34
tctgtccatc agtatgccca ttgcctga                              28

<210> SEQ ID NO 35
<211> LENGTH: 25
<212> TYPE: DNA
<213> ORGANISM: Artificial
<220> FEATURE:
<223> OTHER INFORMATION: Primer

<400> SEQUENCE: 35
caatttgatg ctagcatata tgcac                                 25

<210> SEQ ID NO 36
<211> LENGTH: 30
<212> TYPE: DNA
<213> ORGANISM: Artificial
<220> FEATURE:
<223> OTHER INFORMATION: Primer

<400> SEQUENCE: 36
aatttaaagc aatttctaaa ctgctaaatc                            30

<210> SEQ ID NO 37
<211> LENGTH: 26
<212> TYPE: DNA
<213> ORGANISM: Artificial
<220> FEATURE:
<223> OTHER INFORMATION: Primer

<400> SEQUENCE: 37
agcagatcat actctataaa aacagg                                26

<210> SEQ ID NO 38
<211> LENGTH: 27
<212> TYPE: DNA
<213> ORGANISM: Artificial
<220> FEATURE:
<223> OTHER INFORMATION: Primer

<400> SEQUENCE: 38
gtctattagc aaataagaac tccaatg                               27

<210> SEQ ID NO 39
<211> LENGTH: 24
<212> TYPE: DNA
<213> ORGANISM: Artificial
<220> FEATURE:
<223> OTHER INFORMATION: Primer

<400> SEQUENCE: 39
taaaaggaga aaaggaaga tacg                                   24
```

```
<210> SEQ ID NO 40
<211> LENGTH: 23
<212> TYPE: DNA
<213> ORGANISM: Artificial
<220> FEATURE:
<223> OTHER INFORMATION: Primer

<400> SEQUENCE: 40
attatcttga tgaggatgct ttc                                        23

<210> SEQ ID NO 41
<211> LENGTH: 40
<212> TYPE: DNA
<213> ORGANISM: Artificial
<220> FEATURE:
<223> OTHER INFORMATION: Primer

<400> SEQUENCE: 41
attacatatg tctcatgctt taggtgtagg actttatatc                      40

<210> SEQ ID NO 42
<211> LENGTH: 37
<212> TYPE: DNA
<213> ORGANISM: Artificial
<220> FEATURE:
<223> OTHER INFORMATION: Primer

<400> SEQUENCE: 42
aattggatcc atataaatat ctttcttctt cttcgtc                         37

<210> SEQ ID NO 43
<211> LENGTH: 35
<212> TYPE: DNA
<213> ORGANISM: Artificial
<220> FEATURE:
<223> OTHER INFORMATION: Primer

<400> SEQUENCE: 43
aactcatatg atacctgcta catctgcgaa tattg                           35

<210> SEQ ID NO 44
<211> LENGTH: 36
<212> TYPE: DNA
<213> ORGANISM: Artificial
<220> FEATURE:
<223> OTHER INFORMATION: Primer

<400> SEQUENCE: 44
ttttggatcc acacctttt gaggtatatt taaaac                           36

<210> SEQ ID NO 45
<211> LENGTH: 39
<212> TYPE: DNA
<213> ORGANISM: Artificial
<220> FEATURE:
<223> OTHER INFORMATION: Primer

<400> SEQUENCE: 45
tcttcatatg gctgactttg ttatgggctt tgtaggaag                       39

<210> SEQ ID NO 46
<211> LENGTH: 39
<212> TYPE: DNA
<213> ORGANISM: Artificial
<220> FEATURE:
<223> OTHER INFORMATION: Primer

<400> SEQUENCE: 46
```

-continued tctaggatcc aaatacatac ccatttggaa acctatatc    39

<210> SEQ ID NO 47
<211> LENGTH: 39
<212> TYPE: DNA
<213> ORGANISM: Artificial
<220> FEATURE:
<223> OTHER INFORMATION: Primer

<400> SEQUENCE: 47
tatacatatg tgcggtaata aaacagatac tcaaactac    39

<210> SEQ ID NO 48
<211> LENGTH: 37
<212> TYPE: DNA
<213> ORGANISM: Artificial
<220> FEATURE:
<223> OTHER INFORMATION: Primer

<400> SEQUENCE: 48
attaggatcc tttttaaaaa ctccgctgaa tccatag    37

<210> SEQ ID NO 49
<211> LENGTH: 41
<212> TYPE: DNA
<213> ORGANISM: Artificial
<220> FEATURE:
<223> OTHER INFORMATION: Primer

<400> SEQUENCE: 49
tgttcatatg aaaagcggta ttgagatagg tatatttgtt c    41

<210> SEQ ID NO 50
<211> LENGTH: 35
<212> TYPE: DNA
<213> ORGANISM: Artificial
<220> FEATURE:
<223> OTHER INFORMATION: Primer

<400> SEQUENCE: 50
ggaaggatcc taacacctat ttggaaacct atatc    35

<210> SEQ ID NO 51
<211> LENGTH: 36
<212> TYPE: DNA
<213> ORGANISM: Artificial
<220> FEATURE:
<223> OTHER INFORMATION: Primer

<400> SEQUENCE: 51
tcttcatatg aaaagcggat tcggagttga tttaac    36

<210> SEQ ID NO 52
<211> LENGTH: 35
<212> TYPE: DNA
<213> ORGANISM: Artificial
<220> FEATURE:
<223> OTHER INFORMATION: Primer

<400> SEQUENCE: 52
gaatggatcc cctatttgac cgcctatatc aaatc    35

<210> SEQ ID NO 53
<211> LENGTH: 36
<212> TYPE: DNA
<213> ORGANISM: Artificial

```
<220> FEATURE:
<223> OTHER INFORMATION: Primer

<400> SEQUENCE: 53
ttttcatatg tgtgctacaa cttctaaaag tacatc                                36

<210> SEQ ID NO 54
<211> LENGTH: 36
<212> TYPE: DNA
<213> ORGANISM: Artificial
<220> FEATURE:
<223> OTHER INFORMATION: Primer

<400> SEQUENCE: 54
cctcggatcc gcctttaaag taatagtttt atcatc                                36

<210> SEQ ID NO 55
<211> LENGTH: 35
<212> TYPE: DNA
<213> ORGANISM: Artificial
<220> FEATURE:
<223> OTHER INFORMATION: Primer

<400> SEQUENCE: 55
attacatatg caatttgatg ctagcatata tgcac                                 35

<210> SEQ ID NO 56
<211> LENGTH: 40
<212> TYPE: DNA
<213> ORGANISM: Artificial
<220> FEATURE:
<223> OTHER INFORMATION: Primer

<400> SEQUENCE: 56
tttaggatcc aatttaaagc aatttctaaa ctgctaaatc                            40

<210> SEQ ID NO 57
<211> LENGTH: 34
<212> TYPE: DNA
<213> ORGANISM: Artificial
<220> FEATURE:
<223> OTHER INFORMATION: Primer

<400> SEQUENCE: 57
taaacatatg gtaagagata aatattcaga agag                                  34

<210> SEQ ID NO 58
<211> LENGTH: 39
<212> TYPE: DNA
<213> ORGANISM: Artificial
<220> FEATURE:
<223> OTHER INFORMATION: Primer

<400> SEQUENCE: 58
tattggatcc cctctttat agcttataga agccttaac                              39

<210> SEQ ID NO 59
<211> LENGTH: 41
<212> TYPE: DNA
<213> ORGANISM: Artificial
<220> FEATURE:
<223> OTHER INFORMATION: Primer

<400> SEQUENCE: 59
tttgcatatg aaaacaggat ttgaggttaa tgtattattt c                          41
```

```
<210> SEQ ID NO 60
<211> LENGTH: 38
<212> TYPE: DNA
<213> ORGANISM: Artificial
<220> FEATURE:
<223> OTHER INFORMATION: Primer

<400> SEQUENCE: 60
aaatggatcc ccaatctgag cacctaaatc aacacttg                              38
```

SEQUENCES OF *BRACHYSPIRA*, IMMUNOGENIC COMPOUNDS, METHODS FOR PREPARATION AND USE THEREOF

FIELD

This invention relates to novel genes in *Brachyspira hyodysenteriae* and the proteins encoded therein. This invention further relates to use of these novel genes and proteins for diagnosis of *B. hyodysenteriae* disease, vaccines against *B. hyodysenteriae* and for screening for compounds that kill *B. hyodysenteriae* or block the pathogenic effects of *B. hyodysenteriae*. These sequences may also be useful for diagnostic and therapeutic and/or prophylactic treatment of diseases in animals caused by other *Brachyspira* species, including *B. intermedia, B. alvinipulli, B. aalborgi, B. innocens, B. murdochii*, and *B. pilosicoli*.

BACKGROUND

Swine dysentery is a significant endemic disease of pigs in Australia and worldwide. Swine dysentery is a contagious mucohaemorrhagic diarrhoeal disease, characterised by extensive inflammation and necrosis of the epithelial surface of the large intestine. Economic losses due to swine dysentery result mainly from growth retardation, costs of medication and mortality. The causative agent of swine dysentery was first identified as an anaerobic spirochaete (*Treponema hyodysenteriae*) in 1971, and was recently reassigned to the genus *Brachyspira* as *B. hyodysenteriae*. Where swine dysentery is established in a piggery, the disease spectrum can vary from being mild, transient or unapparent, to being severe and even fatal. Medication strategies on individual piggeries may mask clinical signs and on some piggeries the disease may go unnoticed, or may only be suspected. Whether or not obvious disease occurs, *B. hyodysenteriae* may persist in infected pigs, or in other reservoir hosts such as rodents, or in the environment. All these sources pose potential for transmission of the disease to uninfected herds. Commercial poultry may also be colonized by *B. hyodysenteriae*, although it is not clear how commonly this occurs under field conditions.

Colonisation by *B. hyodysenteriae* elicits a strong immunological response against the spirochaete, hence indirect evidence of exposure to the spirochaete can be obtained by measuring circulating antibody titres in the blood of infected animals. These antibody titres have been reported to be maintained at low levels, even in animals that have recovered from swine dysentery. Serological tests for detection of antibodies therefore have considerable potential for detecting subclinical infections and recovered carrier pigs that have undetectable numbers of spirochaetes in their large intestines. These tests would be particularly valuable in an easy to use kit form, such as an enzyme-linked immunosorbent assay. A variety of techniques have been developed to demonstrate the presence of circulating antibodies against *B. hyodysenteriae*, including indirect fluorescent antibody tests, haemagglutination tests, microtitration agglutination tests, complement fixation tests, and ELISA using either lipopolysaccharide or whole sonicated spirochaetes as antigen. All these tests have suffered from problems of specificity, as related non-pathogenic intestinal spirochaetes can induce cross-reactive antibodies. These tests are useful for detecting herds where there is obvious disease and high circulating antibody titres, but they are problematic for identifying sub-clinically infected herds and individual infected pigs. Consequently, to date, no completely sensitive and specific assays are available for the detection of antibodies against *B. hyodysenteriae*. The lack of suitable diagnostic tests has hampered control of swine dysentery.

A number of methods are employed to control swine dysentery, varying from the prophylactic use of antimicrobial agents, to complete destocking of infected herds and prevention of re-entry of infected carrier pigs. All these options are expensive and, if they are to be fully effective, they require the use of sophisticated diagnostic tests to monitor progress. Currently, detection of swine dysentery in herds with subclinical infections, and individual healthy carrier animals, remains a major problem and is hampering implementation of effective control measures. A definitive diagnosis of swine dysentery traditionally has required the isolation and identification of *B. hyodysenteriae* from the faeces or mucosa of diseased pigs. Major problems involved include the slow growth and fastidious nutritional requirements of these anaerobic bacteria and confusion due to the presence of morphologically similar spirochaetes in the normal flora of the pig intestine. A significant improvement in the diagnosis of individual affected pigs was achieved with the development of polymerase chain reaction (PCR) assays for the detection of spirochaetes from faeces. Unfortunately in practical applications the limit of detection of PCRs rendered it unable to detect carrier animals with subclinical infections. As a consequence of these diagnostic problems, there is a clear need to develop a simple and effective diagnostic tool capable of detecting *B. hyodysenteriae* infection at the herd and individual pig level.

A strong immunological response is induced against the spirochaete following colonization with *B. hyodysenteriae*, and pigs recovered from swine dysentery are protected from re-infection. Despite this, attempts to develop vaccines to control swine dysentery have met with very limited success, either because they have provided inadequate protection on a herd basis, or they have been too costly and difficult to produce to make them commercially viable. Bacterin vaccines provide some level of protection, but they tend to be lipopolysaccharide serogroup-specific, which then requires the use of multivalent bacterins. Furthermore they are difficult and costly to produce on a large scale because of the fastidious anaerobic growth requirements of the spirochaete.

Several attempts have been made to develop attenuated live vaccines for swine dysentery. This approach has the disadvantage that attenuated strains show reduced colonisation, and hence cause reduced immune stimulation. There also is reluctance on the part of producers and veterinarians to use live vaccines for swine dysentery because of the possibility of reversion to virulence, especially as very little is known about genetic regulation and organization in *B. hyodysenteriae*.

The use of recombinant subunit vaccines is an attractive alternative, since the products would be well-defined (essential for registration purposes), and relatively easy to produce on a large scale. To date the first reported use of a recombinant protein from *B. hyodysenteriae* as a vaccine candidate (a 38-kilodalton flagellar protein) failed to prevent colonisation in pigs. This failure is likely to relate specifically to the particular recombinant protein used, as well as to other more down-stream issues of delivery systems and routes, dose rates, choice of adjuvants etc. (Gabe, J D, Chang, R J, Slomiany, R, Andrews, W H and McCaman, M T (1995) Isolation of extracytoplasmic proteins from *Serpulina hyodysenteriae* B204 and molecular cloning of the flaB1 gene encoding a 38-kilodalton flagellar protein. Infection and Immunity 63:142-148). The first reported partially protective recombinant *B. hyodysenteriae* protein used for vaccination was a 29.7 kDa outer membrane lipoprotein (Bhlp29.7, also referred to as BmpB and BlpA) which had homology with the methionine-binding lipoproteins of various pathogenic bacteria. The use of the his-tagged recombinant Bhlp29.7 protein for vaccination of pigs, followed by experimental challenge with *B. hyodysenteriae*, resulted in 17-40% of vaccinated pigs developing disease compared to 50-70% of the unvaccinated control pigs developing disease. Since the incidence of disease for the Bhlp29.7 vaccinated pigs was significantly (P=0.047) less than for the control pigs, Bhlp29.7 appeared to have potential as a swine dysentery vaccine component (La, T, Phillips, N D, Reichel, M P and Hampson, D J (2004). Protection of pigs from swine dysentery by vaccination with recombinant BmpB, a 29.7 kDa outer-membrane lipoprotein of *Brachyspira hyodysenteriae*. Veterinary Microbiology 102:97-109). A number of other attempts have been made to identify outer envelop proteins from *B. hyodysenteriae* that could be used as recombinant vaccine components, but again no successful vaccine has yet been made. A much more global approach is needed to the identification of potentially useful immunogenic recombinant proteins from *B. hyodysenteriae* is needed.

To date, only one study using DNA for vaccination has been reported. In this study, the *B. hyodysenteriae* ftnA gene, encoding a putative ferritin, was cloned into an *E. coli* plasmid and the plasmid DNA used to coat gold beads for ballistic vaccination. A murine model for swine dysentery was used to determine the protective nature of vaccination with DNA and/or recombinant protein. Vaccination with recombinant protein induced a good systemic response against ferritin however vaccination with DNA induced only a detectable systemic response. Vaccination with DNA followed a boost with recombinant protein induced a systemic immune response to ferritin only after boosting with protein. However, none of the vaccination regimes tested was able to provide the mice with protection against *B. hyodysenteriae* colonisation and the associated lesions. Interestingly, vaccination of the mice with DNA alone resulted in significant exacerbation of disease (Davis, A. J., Smith, S. C. and Moore, R. J. (2005). The *Brachyspira hyodysenteriae* ftnA gene: DNA vaccination and real-time PCR quantification of bacteria in a mouse model of disease. Current Microbiology 50: 285-291).

SUMMARY

Inventors have identified novel genes from *B. hyodysenteriae* and the proteins encoded by those genes. They have further identified that these novel genes and proteins can be used for therapeutic and diagnostic purposes. Moreover, the inventors have identified that these genes and/or the proteins can be used as a vaccine against *B. hyodysenteriae* and/or diagnose *B. hyodysenteriae* infections. Accordingly, in a first aspect, the present invention provides an isolated polynucleotide comprising a nucleotide sequence selected from the group consisting of SEQ ID NO: 1, 3, 5, 7, 9, 11, 13, 15, 17, and 19. The present invention also provides nucleotide sequences that are homologous to SEQ ID NOs: 1, 3, 5, 7, 9, 11, 13, 15, 17, and 19, where the homology can be 95%, 90%, 85%, 80%, 75% and 70%. This invention also includes a DNA vaccine or DNA immunogenic composition containing the nucleotide sequence of SEQ ID NOs: 1, 3, 5, 7, 9, 11, 13, 15, 17, and 19 and sequences that are 95%, 90%, 85%, 80%, 75% and 70% homologous to these sequences. This invention further includes a diagnostic assay containing DNA having the nucleotide sequence of SEQ ID NOs: 1, 3, 5, 7, 9, 11, 13, 15, 17, and 19, and sequences that are 95%, 90%, 85%, 80%, 75% and 70% homologous to these sequences.

In one aspect of the invention, the vaccine composition is a vaccine composition comprising at least two polynucleotides encoding molecules selected from the group consisting of SEQ ID No. 1, 3, 5 and 7 for the treatment or prevention of swine dysentery associated with *Brachyspira hyodysenteriae*.

In another aspect of the invention, the vaccine composition is a vaccine composition comprising at least three polynucleotides encoding molecules selected from the group consisting of SEQ ID No. 1, 3, 5 and 7 for the treatment or prevention of swine dysentery associated with *Brachyspira hyodysenteriae*.

In yet another aspect of the invention, the vaccine composition is a vaccine composition consisting of polynucleotides encoding molecules selected from the group consisting of: SEQ ID No. 1, 3, 5 and 7 for the treatment or prevention of swine dysentery associated with *Brachyspira hyodysenteriae*.

In a further aspect of the invention, the vaccine composition is a vaccine composition comprising at least two polynucleotides encoding molecules selected from the group consisting of SEQ ID No. 9, 11, 13 and 15 for the treatment or prevention of swine dysentery associated with *Brachyspira hyodysenteriae*.

In another aspect of the invention, the vaccine composition is a vaccine composition comprising at least three polynucleotides encoding molecules selected from the group consisting of SEQ ID No. 9, 11, 13 and 15 for the treatment or prevention of swine dysentery associated with *Brachyspira hyodysenteriae*.

In yet another aspect of the invention, the vaccine composition is a vaccine composition consisting of polynucleotides encoding molecules selected from the group consisting of: SEQ ID No. 9, 11, 13 and 15 for the treatment or prevention of swine dysentery associated with *Brachyspira hyodysenteriae*.

In a further aspect of the invention, the vaccine composition is a vaccine composition comprising at least two polynucleotides encoding molecules selected from the group consisting of SEQ ID No. 17, and 19 for the treatment or prevention of swine dysentery associated with *Brachyspira hyodysenteriae*.

In another aspect of the invention, the vaccine composition is a vaccine composition comprising:
(i) at least one polynucleotide encoding a molecule selected from the group of: SEQ ID No. 1, 3, 5 and 7; and/or
(ii) at least one polynucleotide encoding a molecule selected from the group of: SEQ ID No. 9, 11, 13 and 15 and/or
(iii) at least one polynucleotide encoding a molecule selected from the group of: SEQ ID No. 17 and for the treatment or prevention of swine dysentery associated with *Brachyspira*.

The present invention also provides plasmids containing DNA having the sequence of SEQ ID NOs: 1, 3, 5, 7, 9, 11, 13, 15, 17, and 19; prokaryotic and/or eukaryotic expression vectors containing DNA having the sequence of SEQ ID NOs: 1, 3, 5, 7, 9, 11, 13, 15, 17, and 19; and a cell containing the plasmids which contain DNA having the sequence of SEQ ID NOs: 1, 3, 5, 7, 9, 11, 13, 15, 17, and 19.

In a second aspect, the present invention provides an isolated polypeptide comprising the amino acid sequence selected from the group consisting of SEQ ID NO: 2, 4, 6, 8, 10, 12, 14, 16, 18, and 20. The present invention also provides novel *B. hyodysenteriae* proteins having the amino acid sequence contained in SEQ ID NOs: 2, 4, 6, 8, 10, 12, 14, 16, 18, and 20. This invention also provides proteins that are 95%, 90%, 85%, 80%, 75% and 70% homologous to the sequences contained in SEQ ID NOs: 2, 4, 6, 8, 10, 12, 14, 16, 18, and 20. The present invention also provides a vaccine or immunogenic composition to contain the proteins having the amino acid sequence contained in SEQ ID NOs: 2, 4, 6, 8, 10, 12, 14, 16, 18, and 20 or amino acid sequences that are 95%, 90%, 85%, 80%, 75% and 70% homologous to the sequences contained in SEQ ID NOs: 2, 4, 6, 8, 10, 12, 14, 16, 18, and 20.

In one aspect of the invention, the vaccine composition is a vaccine composition comprising at least two polypeptides selected from the group consisting of SEQ ID No. 2, 4, 6 and 8 for the treatment or prevention of swine dysentery associated with *Brachyspira hyodysenteriae*.

In another aspect of the invention, the vaccine composition is a vaccine composition comprising at least three polypeptides selected from the group consisting of SEQ ID No. 2, 4, 6 and 8 for the treatment or prevention of swine dysentery associated with *Brachyspira hyodysenteriae*.

In yet another aspect of the invention, the vaccine composition is a vaccine composition consisting of polypeptides SEQ ID No. 2, 4, 6 and 8 for the treatment or prevention of swine dysentery associated with *Brachyspira hyodysenteriae*.

In one aspect of the invention, the vaccine composition is a vaccine composition comprising at least two polypeptides selected from the group consisting of SEQ ID No. 10, 12, 14 and 16 for the treatment or prevention of swine dysentery associated with *Brachyspira hyodysenteriae*.

In another aspect of the invention, the vaccine composition is a vaccine composition comprising at least three polypeptides selected from the group consisting of SEQ ID No. 10, 12, 14 and 16 for the treatment or prevention of swine dysentery associated with *Brachyspira hyodysenteriae*.

In yet another aspect of the invention, the vaccine composition is a vaccine composition consisting of polypeptides from the group consisting of: SEQ ID No. 10, 12, 14 and 16 for the treatment or prevention of swine dysentery associated with *Brachyspira hyodysenteriae*.

In one aspect of the invention, the vaccine composition is a vaccine composition comprising at least two polypeptides selected from the group consisting of SEQ ID No. 18 and 20 for the treatment or prevention of swine dysentery associated with *Brachyspira hyodysenteriae*.

In a further aspect of the invention, the vaccine composition is a vaccine composition comprising:
(i) at least one polypeptide selected from the group of: SEQ ID No. 2, 4, 6, or 8 and/or
(ii) at least one polypeptide selected from the group of: SEQ ID No. 10, 12, 14, or 16 and/or
(iii) at least one selected from the group of: SEQ ID No. 18 and 20 for the treatment or prevention of swine dysentery associated with *Brachyspira hyodysenteriae*.

In a third aspect, the present invention provides a method of diagnosing *Brachyspira* infection comprising: (a) providing a sample from an animal suspected of being infected with *Brachyspira*; (b) contacting the sample with one or more polypeptides comprising the amino acid sequence selected from the group consisting of SEQ ID NO: 2, 4, 6, 8, 10, 12, 14, 16, 18, and 20; (c) incubating the sample and polypeptide under conditions which allow for the formation of antibody-antigen complexes; and (d) determining whether an antibody-antigen complex with one or more polypeptides is formed, wherein the formation of an antibody-antigen complex indicates the animal is infected with *Brachyspira*.

In a fourth aspect, the present invention provides a kit for diagnosing *Brachyspira* infection comprising one or more polypeptides comprising the amino acid sequence selected from the group consisting of SEQ ID NO: 2, 4, 6, 8, 10, 12, 14, 16, 18, and 20.

It is a further aspect of this invention to have a diagnostic kit containing one or more proteins having a sequence contained in SEQ ID NOs: 2, 4, 6, 8, 10, 12, 14, 16, 18 and 20 or that are 95%, 90%, 85%, 80%, 75% and 70% homologous to the sequences contained in SEQ ID NOs: 2, 4, 6, 8, 10, 12, 14, 16, 18, and 20.

It is another aspect of this invention to have nucleotide sequences which encode the proteins having the amino acid sequence contained in SEQ ID NOs: 2, 4, 6, 8, 10, 12, 14, 16, 18, and 20. The invention also covers plasmids, eukaryotic and prokaryotic expression vectors, and DNA vaccines which contain DNA having a sequence which encodes a protein having the amino acid sequence contained in SEQ ID NOs: 2, 4, 6, 8, 10, 12, 14, 16, 18, and 20. Cells which contain these plasmids and expression vectors are included in this invention.

This invention includes monoclonal antibodies that bind to proteins having an amino acid sequence contained in SEQ ID NOs: 2, 4, 6, 8, 10, 12, 14, 16, 18, and 20 or bind to proteins that are 95%, 90%, 85%, 80%, 75% and 70% homologous to the sequences contained in SEQ ID NOs: 2, 4, 6, 8, 10, 12, 14, 16, 18, and 20. Diagnostic kits containing the monoclonal antibodies that bind to proteins having an amino acid sequence contained in SEQ ID NOs: 2, 4, 6, 8, 10, 12, 14, 16, 18, and 20 or bind to proteins that are 95%, 90%, 85%, 80%, 75% and 70% homologous to the sequences contained in SEQ ID NOs: 2, 4, 6, 8, 10, 12, 14, 16, 18, and 20 are included in this invention. These diagnostic kits can detect the presence of *B. hyodysenteriae* in an animal. The animal is preferably a mammal or a bird; more preferably, chicken, goose, duck, turkey, parakeet, dog, cat, hamster, gerbil, rabbit, ferret, horse, cow, sheep, pig, monkey, and human.

The invention also contemplates the method of preventing or treating an infection of *B. hyodysenteriae* in an animal by administering to an animal a DNA vaccine containing one or more nucleotide sequences listed in SEQ ID NOs: 1, 3, 5, 7, 9, 11, 13, 15, 17, and 19 or sequences that are 95%, 90%, 85%, 80%, 75% and 70% homologous to these sequences. This invention also covers a method of preventing or treating an infection of *B. hyodysenteriae* in an animal by administering to an animal a vaccine containing one or more proteins having the amino acid sequence containing in SEQ ID NOs: 2, 4, 6, 8, 10, 12, 14, 16, 18, and 20 or sequences that are 95%, 90%, 85%, 80%, 75% and 70% homologous to these sequences.

The invention also contemplates the method of generating an immune response in an animal by administering to an animal an immunogenic composition containing one or more nucleotide sequences listed in SEQ ID NOs: 1, 3, 5, 7, 9, 11, 13, 15, 17, and 19 or sequences that are 95%, 90%, 85%, 80%, 75% and 70% homologous to these sequences. This invention also covers a method of generating an immune response in an animal by administering to an animal an immunogenic composition containing one or more proteins having the amino acid sequence containing in SEQ ID NOs: 2, 4, 6, 8, 10, 12, 14, 16, 18, and 20 or sequences that are 95%, 90%, 85%, 80%, 75% and 70% homologous to these sequences.

DETAILED DESCRIPTION OF THE PREFERRED EMBODIMENTS OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional immunological and molecular biological techniques and pharmacology within the skill of the art. Such techniques are well known to the skilled worker, and are explained fully in the literature. See, eg., Coligan, Dunn, Ploegh, Speicher and Wingfield "Current protocols in Protein Science" (1999) Volume I and II (John Wiley & Sons Inc.); Sambrook et al., "Molecular Cloning: A Laboratory Manual" (1989), $2^{nd}$ Edition (Cold Spring Harbor Laboratory press); and Prescott, Harley and Klein "Microbiology" (1999), $4^{th}$ Edition (WBC McGraw-Hill).

It must be noted that as used herein and in the appended claims, the singular forms "a," "an," and "the" include plural reference unless the context clearly dictates otherwise. Thus, for example, a reference to "a gene" includes a plurality of such genes, and a reference to "an animal" is a reference to one or more animals, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In the broadest aspect of the invention there is provided a novel *B. hyodysenteriae* polynucleotide having the nucleotide sequence contained in SEQ ID NOs: 1, 3, 5, 7, 9, 11, 13, 15, 17, 19, 21 and 23 or an amino acid sequence (polypeptide) encoded by these polynucleotides.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

An animal can be a mammal or a bird that can be infected with *Brachyspira*, especially *B. hyodysenteriae*. Examples of mammals include dog, cat, hamster, gerbil, rabbit, ferret, horse, cow, sheep, pig, monkey, and human. Examples of birds include chicken, goose, duck, turkey, and parakeet. It is appreciated by those skilled in the art that certain *Brachyspira* species are capable of infecting a broad host range (see, for example, Hampson et al., 2006, Emerging Infectious diseases, Vol. 12(5), p 869-870, incorporated herein in its entirety by reference). Accordingly the term "animal" as used herein encompasses a range of animals, but especially pigs and poultry.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schinner., Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). Examples of amino acid groups defined in this manner include: (i) a positively-charged group containing Lys, Arg and His, (ii) a negatively-charged group containing Glu and Asp, (iii) an aromatic group containing Phe, Tyr and Trp, (iv) a nitrogen ring group containing His and Trp, (v) a large aliphatic nonpolar group containing Val, Leu and De, (vi) a slightly-polar group containing Met and Cys, (vii) a small-residue group containing Ser, Thr, Asp, Asn, Gly, Ala, Glu, Gln and Pro, (viii) an aliphatic group containing Val, Leu, Ile, Met and Cys, and (ix) a small, hydroxyl group containing Ser and Thr.

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The polynucleotide sequences encoding the fusion protein may be operably linked in frame so that the fusion protein may be translated correctly. A fusion protein may include polypeptide sequences from the same species or from different species. In various embodiments, the fusion polypeptide may contain one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides containing a glutathione S-transferase tag (GST-tag), histidine tag (His-tag), an immunoglobulin domain or an immunoglobulin binding domain.

The term "isolated polypeptide" refers to a polypeptide, in certain embodiments prepared from recombinant DNA or RNA, or of synthetic origin or natural origin, or some combination thereof, which (1) is not associated with proteins that it is normally found with in nature, (2) is separated from the cell in which it normally occurs, (3) is free of other proteins from the same cellular source, (4) is expressed by a cell from a different species, or (5) does not occur in nature. It is possible for an isolated polypeptide to exist, but not qualify as a purified polypeptide.

The term "isolated nucleic acid" and "isolated polynucleotide" refers to a polynucleotide whether genomic DNA, cDNA, mRNA, tRNA, rRNA, iRNA, or a polynucleotide obtained from a cellular organelle (such as mitochondria and chloroplast), or whether from synthetic origin, which (1) is not associated with the cell in which the "isolated nucleic acid" is found in nature, or (2) is operably linked to a polynucleotide to which it is not linked in nature. It is possible for an isolated polynucleotide to exist, but not qualify as a purified polynucleotide.

The term "nucleic acid" and "polynucleotide" refers to a polymeric form of nucleotides, either ribonucleotides or deoxyribonucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" and "polynucleotide of the invention" refers to a nucleic acid encoding a polypeptide of the invention. A polynucleotide of the invention may comprise all, or a portion of, a subject nucleic acid sequence; a nucleotide sequence at least 60%, 70%, 80%, 90%, 95%, 96%, 97%, 98% or 99% identical to a subject nucleic acid sequence; a nucleotide sequence that hybridizes under stringent conditions to a subject nucleic acid sequence; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous or identical with a subject amino acid sequence; nucleotide sequences encoding polypeptides having an activity of a polypeptide of the invention and having at least about 60%, 70%, 80%, 85%, 90%, 95%, 98%, 99% or more homology or identity with a subject amino acid sequence; nucleotide sequences that differ by 1 to about 2, 3, 5, 7, 10, 15, 20, 30, 50, 75 or more nucleotide substitutions, additions or deletions, such as allelic variants, of a subject nucleic acid sequence; nucleic acids derived from and evolutionarily related to a subject nucleic acid sequence; and complements of, and nucleotide sequences resulting from the degeneracy of the genetic code, for all of the foregoing and other nucleic acids of the invention. Nucleic acids of the invention also include homologs, e.g., orthologs and paralogs, of a subject nucleic acid sequence and also variants of a subject nucleic acid sequence which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a domain having the desired biological activity, and optionally additional amino acids on one or both sides of the domain, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide containing a subject amino acid sequence, or an equivalent or fragment thereof. Polypeptides of the invention include polypeptides containing all or a portion of a subject amino acid sequence; a subject amino acid sequence with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to a subject amino acid sequence; and functional fragments thereof. Polypeptides of the invention also include homologs, e.g., orthologs and paralogs, of a subject amino acid sequence.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

The term "purified" refers to an object species that is the predominant species present (i.e., on a molar basis it is more abundant than any other individual species in the composition). A "purified fraction" is a composition wherein the object species is at least about 50 percent (on a molar basis) of all species present. In making the determination of the purity or a species in solution or dispersion, the solvent or matrix in which the species is dissolved or dispersed is usually not included in such determination; instead, only the species (including the one of interest) dissolved or dispersed are taken into account. Generally, a purified composition will have one species that is more than about 80% of all species present in the composition, more than about 85%, 90%, 95%, 99% or more of all species present. The object species may be purified to essential homogeneity (contaminant species cannot be detected in the composition by conventional detection methods) wherein the composition is essentially a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase (e.g., Pho5), the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids or nucleotides occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups).

The solubility of polypeptides may be measured using a variety of art recognized techniques, including dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams of more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions which promote specific hybridization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C.

However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((3 \times \#GC)+(2 \times \#AT)) \times 37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution containing 50% formamide, 10×Denhardt (0.2% Ficoll, 0.2% polyvinylpyrrolidone, 0.2% bovine serum albumin) and 200 µg/ml of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y.; S. Agrawal (ed.) Methods in Molecular Biology, volume 20; Tijssen (1993) Laboratory Techniques in Biochemistry and Molecular Biology—Hybridization With Nucleic Acid Probes, e.g., part I chapter 2 "Overview of principles of hybridization and the strategy of nucleic acid probe assays", Elsevier, New York; and Tibanyenda, N. et al., Eur. J. Biochem. 139:19 (1984) and Ebel, S. et al., Biochem. 31:12083 (1992).

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The nucleic acids of the invention may be used as diagnostic reagents to detect the presence or absence of the target DNA or RNA sequences to which they specifically bind, such as for determining the level of expression of a nucleic acid of the invention. In one aspect, the present invention contemplates a method for detecting the presence of a nucleic acid of the invention or a portion thereof in a sample, the method of the steps of: (a) providing an oligonucleotide at least eight nucleotides in length, the oligonucleotide being complementary to a portion of a nucleic acid of the invention; (b) contacting the oligonucleotide with a sample containing at least one nucleic acid under conditions that permit hybridization of the oligonucleotide with a nucleic acid of the invention or a portion thereof; and (c) detecting hybridization of the oligonucleotide to a nucleic acid in the sample, thereby detecting the presence of a nucleic acid of the invention or a portion thereof in the sample. In another aspect, the present invention contemplates a method for detecting the presence of a nucleic acid of the invention or a portion thereof in a sample, by (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample containing at least one nucleic acid under hybridization conditions; (c) amplifying the nucleotide sequence between the two oligonucleotide primers; and (d) detecting the presence of the amplified sequence, thereby detecting the presence of a nucleic acid of the invention or a portion thereof in the sample.

In another aspect of the invention, the polynucleotide of the invention is provided in an expression vector containing a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

An expression vector containing the polynucleotide of the invention can then be used as a pharmaceutical agent to treat an animal infected with B. hyodysenteriae or as a vaccine (also a pharmaceutical agent) to prevent an animal from being infected with B. hyodysenteriae, or to reduce the symptoms and course of the disease if the animal does become infected. One manner of using an expression vector as a pharmaceutical agent is to administer a nucleic acid vaccine to the animal at risk of being infected or to the animal after being infected. Nucleic acid vaccine technology is well-described in the art. Some descriptions can be found in U.S. Pat. No. 6,562,376 (Hooper et al.); U.S. Pat. No. 5,589,466 (Felgner, et al.); U.S. Pat. No. 6,673,776 (Felgner, et al.); and U.S. Pat. No. 6,710,035 (Felgner, et al.). Nucleic acid vaccines can be injected into muscle or intradermally, can be electroporated into the animal (see WO 01/23537, King et al.; and WO 01/68889, Malone et al.), via lipid compositions (see U.S. Pat. No. 5,703,055, Felgner, et al), or other mechanisms known in the art field.

Expression vectors can also be transfected into bacteria which can be administered to the target animal to induce an immune response to the protein encoded by the nucleotides of this invention contained on the expression vector. The expression vector can contain eukaryotic expression sequences such that the nucleotides of this invention are transcribed and translated in the host animal. Alternatively, the expression vector can be transcribed in the bacteria and then translated in the host animal. The bacteria used as a carrier of the expression vector should be attenuated but still invasive. One can use *Shigella* spp., *Salmonella* spp., *Escherichia* spp., and *Aeromonas* spp., just to name a few, that have been attenuated but still invasive. Examples of these methods can be found in U.S. Pat. No. 5,824,538 (Branstrom et al); U.S. Pat. No. 5,877,159 (Powell, et al.); U.S. Pat. No. 6,150,170 (Powell, et al.); U.S. Pat. No. 6,500,419 (Hone, et al.); and U.S. Pat. No. 6,682,729 (Powell, et al.).

Alternatively, the polynucleotides of this invention can be placed in certain viruses which act a vector. Viral vectors can either express the proteins of this invention on the surface of the virus, or carry polynucleotides of this invention into an animal cell where the polynucleotide is transcribed and translated into a protein. The animal infected with the viral vectors can develop an immune response to the proteins encoded by the polynucleotides of this invention. Thereby one can alleviate or prevent an infection by *B. hyodysenteriae* in the animal which received the viral vectors. Examples of viral vectors can be found U.S. Pat. No. 5,283,191 (Morgan et al.); U.S. Pat. No. 5,554,525 (Sondermeijer et al) and U.S. Pat. No. 5,712,118 (Murphy).

The polynucleotide of the invention may be used to cause expression and over-expression of a polypeptide of the invention in cells propagated in culture, e.g. to produce proteins or polypeptides, including fusion proteins or polypeptides.

This invention pertains to a host cell transfected with a recombinant gene in order to express a polypeptide of the invention. The host cell may be any prokaryotic or eukaryotic cell. For example, a polypeptide of the invention may be expressed in bacterial cells, such as *E. coli*, insect cells (baculovirus), yeast, plant, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Alternatively, the nucleotide sequence may be altered to optimize expression in the host cell, yet the protein produced would have high homology to the originally encoded protein. Other methods suitable for maximizing expression of the polypeptide will be known to those in the art.

The present invention further pertains to methods of producing the polypeptides of the invention. For example, a host cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Suitable vectors for the expression of a polypeptide of the invention include plasmids of the types: pTrcHis-derived plasmids, pET-derived plasmids, pBR322-derived plasmids, pEMBL-derived plasmids, pEX-derived plasmids, pBTac-derived plasmids and pUC-derived plasmids for expression in prokaryotic cells, such as *E. coli*. The various methods employed in the preparation of the plasmids and transformation of host organisms are well known in the art. For other suitable expression systems for both prokaryotic and eukaryotic cells, as well as general recombinant procedures, see *Molecular Cloning, A Laboratory Manual*, 2nd Ed., ed. by Sambrook, Fritsch and Maniatis (Cold Spring Harbor Laboratory Press, 1989) Chapters 16 and 17.

Coding sequences for a polypeptide of interest may be incorporated as a part of a fusion gene including a nucleotide sequence encoding a different polypeptide. The present invention contemplates an isolated polynucleotide containing a nucleic acid of the invention and at least one heterologous sequence encoding a heterologous peptide linked in frame to the nucleotide sequence of the nucleic acid of the invention so as to encode a fusion protein containing the heterologous polypeptide. The heterologous polypeptide may be fused to (a) the C-terminus of the polypeptide of the invention, (b) the N-terminus of the polypeptide of the invention, or (c) the C-terminus and the N-terminus of the polypeptide of the invention. In certain instances, the heterologous sequence encodes a polypeptide permitting the detection, isolation, solubilization and/or stabilization of the polypeptide to which it is fused. In still other embodiments, the heterologous sequence encodes a polypeptide such as a poly His tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

In other embodiments, the invention provides for nucleic acids of the invention immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array. The array may contain one or more polynucleotides of the invention as described herein. In one embodiment, the chip contains one or more polynucleotides of the invention as part of an array of polynucleotide sequences from the same pathogenic species as such polynucleotide(s).

In a preferred form of the invention there is provided isolated *B. hyodysenteriae* polypeptides as herein described, and also the polynucleotide sequences encoding these polypeptides. More desirably the *B. hyodysenteriae* polypeptides are provided in substantially purified form.

Preferred polypeptides of the invention will have one or more biological properties (e.g., in vivo, in vitro or immunological properties) of the native full-length polypeptide. Non-functional polypeptides are also included within the scope of the invention because they may be useful, for example, as antagonists of the functional polypeptides. The biological properties of analogues, fragments, or derivatives relative to wild type may be determined, for example, by means of biological assays.

Polypeptides, including analogues, fragments and derivatives, can be prepared synthetically (e.g., using the well known techniques of solid phase or solution phase peptide synthesis). Preferably, solid phase synthetic techniques are employed. Alternatively, the polypeptides of the invention can be prepared using well known genetic engineering techniques, as described infra. In yet another embodiment, the polypeptides can be purified (e.g., by immunoaffinity purification) from a biological fluid, such as but not limited to plasma, faeces, serum, or urine from animals, including, but not limited to, pig, chicken, goose, duck, turkey, parakeet, human, monkey, dog, cat, horse, hamster, gerbil, rabbit, ferret, horse, cattle, and sheep.

The *B. hyodysenteriae* polypeptide analogues include those polypeptides having the amino acid sequence, wherein one or more of the amino acids are substituted with another amino acid which substitutions do not substantially alter the biological activity of the molecule.

According to the invention, the polypeptides of the invention produced recombinantly or by chemical synthesis and fragments or other derivatives or analogues thereof, including fusion proteins, may be used as an immunogen to generate antibodies that recognize the polypeptides.

A molecule is "antigenic" when it is capable of specifically interacting with an antigen recognition molecule of the immune system, such as an immunoglobulin (antibody) or T cell antigen receptor. An antigenic amino acid sequence contains at least about 5, and preferably at least about 10, amino acids. An antigenic portion of a molecule can be the portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567, as well as antigen binding portions of antibodies, including Fab, $F(ab')_2$ and F(v) (including single chain antibodies). Accordingly, the phrase "antibody molecule" in its various grammatical forms as used herein contemplates both an intact immunoglobulin molecule and an immunologically active portion of an immunoglobulin molecule containing the antibody combining site. An "antibody combining site" is that structural portion of an antibody molecule comprised of heavy and light chain variable and hypervariable regions that specifically binds an antigen.

Exemplary antibody molecules are intact immunoglobulin molecules, substantially intact immunoglobulin molecules and those portions of an immunoglobulin molecule that contain the paratope, including those portions known in the art as Fab, Fab', $F(ab')_2$ and F(v), which portions are preferred for use in the therapeutic methods described herein.

Fab and $F(ab')_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from $F(ab')_2$ portions followed by reduction with mercaptoethanol of the disulfide bonds linking the two heavy chain portions, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The term "adjuvant" refers to a compound or mixture that enhances the immune response to an antigen. An adjuvant can serve as a tissue depot that slowly releases the antigen and also as a lymphoid system activator that non-specifically enhances the immune response [Hood et al., in *Immunology*, p. 384, Second Ed., Benjamin/Cummings, Menlo Park, Calif. (1984)]. Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminium hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

Various procedures known in the art may be used for the production of polyclonal antibodies to the polypeptides of the invention. For the production of antibody, various host animals can be immunised by injection with the polypeptide of the invention, including but not limited to rabbits, mice, rats, sheep, goats, etc. In one embodiment, a polypeptide of the invention can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole Limpet hemocyanins, dinitrophenol, and potentially useful human adjuvants such as BCG (bacille Calmette-Guerin) and *Corynebacterium parvum*.

For preparation of monoclonal antibodies directed toward a polypeptide of the invention, any technique that provides for the production of antibody molecules by continuous cell lines in culture may be used. These include but are not limited to the hybridoma technique originally developed by Kohler et al., (1975) *Nature,* 256:495-497, the trioma technique, the human B-cell hybridoma technique [Kozbor et al., (1983) *Immunology Today,* 4:72], and the EBV-hybridoma technique to produce human monoclonal antibodies [Cole et al., (1985) in *Monoclonal Antibodies and Cancer Therapy*, pp. 77-96, Alan R. Liss, Inc.]. Immortal, antibody-producing cell lines can be created by techniques other than fusion, such as direct transformation of B lymphocytes with oncogenic DNA, or transfection with Epstein-Barr virus. See, e.g., U.S. Pat. Nos. 4,341,761; 4,399,121; 4,427,783; 4,444,887; 4,451,570; 4,466,917; 4,472,500; 4,491,632; and 4,493,890.

In an additional embodiment of the invention, monoclonal antibodies can be produced in germ-free animals utilising recent technology. According to the invention, chicken or swine antibodies may be used and can be obtained by using chicken or swine hybridomas or by transforming B cells with EBV virus in vitro. In fact, according to the invention, techniques developed for the production of "chimeric antibodies" [Morrison et al., (1984) *J. Bacteriol.,* 159-870; Neuberger et al., (1984) *Nature,* 312:604-608; Takeda et al., (1985) *Nature,* 314:452-454] by splicing the genes from a mouse antibody molecule specific for a polypeptide of the invention together with genes from an antibody molecule of appropriate biological activity can be used; such antibodies are within the scope of this invention. Such chimeric antibodies are preferred for use in therapy of intestinal diseases or disorders (described infra), since the antibodies are much less likely than xenogenic antibodies to induce an immune response, in particular an allergic response, themselves.

According to the invention, techniques described for the production of single chain antibodies (U.S. Pat. No. 4,946,778) can be adapted to produce single chain antibodies specific for an polypeptide of the invention. An additional embodiment of the invention utilises the techniques described for the construction of Fab expression libraries [Huse et al.,  (1989) *Science,* 246:1275-1281] to allow rapid and easy identification of monoclonal Fab fragments with the desired specificity for a polypeptide of the invention.

Antibody fragments, which contain the idiotype of the antibody molecule, can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA, "sandwich" immunoassays, immunoradiometric assays, gel diffusion precipitin reactions, immunodiffusion assays, in situ immunoassays (using colloidal gold, enzyme or radioisotope labels, for example), Western blots, precipitation reactions, agglutination assays (e.g., gel agglutination assays, hemagglutination assays), complement fixation assays, immunofluorescence assays, protein A assays, immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are within the scope of the present invention. For example, to select antibodies that recognise a specific epitope of a polypeptide of the invention, one may assay generated hybridomas for a product that binds to a fragment of a polypeptide of the invention containing such epitope.

The invention also covers diagnostic and prognostic methods to detect the presence of *B. hyodysenteriae* using a polypeptide of the invention and/or antibodies which bind to the polypeptide of the invention and kits useful for diagnosis and prognosis of *B. hyodysenteriae* infections.

Diagnostic and prognostic methods will generally be conducted using a biological sample obtained from an animal, such as chicken or swine. A "sample" refers to an animal's tissue or fluid suspected of containing a *Brachyspira* species, such as *B. hyodysenteriae*, or its polynucleotides or its polypeptides. Examples of such tissue or fluids include, but not limited to, plasma, serum, faecal material, urine, lung, heart, skeletal muscle, stomach, intestines, and in vitro cell culture constituents.

The invention provides methods for detecting the presence of a polypeptide of the invention in a sample, with the following steps: (a) contacting a sample suspected of containing a polypeptide of the invention with an antibody (preferably bound to a solid support) that specifically binds to the polypeptide of the invention under conditions which allow for the formation of reaction complexes comprising the antibody and the polypeptide of the invention; and (b) detecting the formation of reaction complexes comprising the antibody and polypeptide of the invention in the sample, wherein detection of the formation of reaction complexes indicates the presence of the polypeptide of the invention in the sample.

Preferably, the antibody used in this method is derived from an affinity-purified polyclonal antibody, and more preferably a monoclonal antibody. In addition, it is preferable for the antibody molecules used herein be in the form of Fab, Fab', F(ab')$_2$ or F(v) portions or whole antibody molecules.

Particularly preferred methods for detecting *B. hyodysenteriae* based on the above method include enzyme linked immunosorbent assays, radioimmunoassays, immunoradiometric assays and immunoenzymatic assays, including sandwich assays using monoclonal and/or polyclonal antibodies.

Three such procedures that are especially useful utilise either polypeptide of the invention (or a fragment thereof) labelled with a detectable label, antibody $Ab_1$ labelled with a detectable label, or antibody $Ab_2$ labelled with a detectable label. The procedures may be summarized by the following equations wherein the asterisk indicates that the particle is labelled and "AA" stands for the polypeptide of the invention:

$$AA^* + Ab_1 = AA^*Ab_1 \quad\quad\quad A.$$

$$AA + Ab^*_1 = AAAb_1^* \quad\quad\quad B.$$

$$AA + Ab_1 + Ab_2^* = Ab_1 AAAb_2^* \quad\quad\quad C.$$

The procedures and their application are all familiar to those skilled in the art and accordingly may be utilised within the scope of the present invention. The "competitive" procedure, Procedure A, is described in U.S. Pat. Nos. 3,654,090 and 3,850,752. Procedure B is representative of well-known competitive assay techniques. Procedure C, the "sandwich" procedure, is described in U.S. Pat. Nos. RE 31,006 and 4,016,043. Still other procedures are known, such as the "double antibody" or "DASP" procedure, and can be used.

In each instance, the polypeptide of the invention form complexes with one or more antibody(ies) or binding partners and one member of the complex is labelled with a detectable label. The fact that a complex has formed and, if desired, the amount thereof, can be determined by known methods applicable to the detection of labels.

It will be seen from the above, that a characteristic property of $Ab_2$ is that it will react with $Ab_1$. This reaction is because $Ab_1$, raised in one mammalian species, has been used in another species as an antigen to raise the antibody, $Ab_2$. For example, $Ab_2$ may be raised in goats using rabbit antibodies as antigens. $Ab_2$ therefore would be anti-rabbit antibody raised in goats. For purposes of this description and claims, $Ab_1$ will be referred to as a primary antibody, and $Ab_2$ will be referred to as a secondary or anti-$Ab_1$ antibody.

The labels most commonly employed for these studies are radioactive elements, enzymes, chemicals that fluoresce when exposed to ultraviolet light, and others. Examples of fluorescent materials capable of being utilised as labels include fluorescein, rhodamine and auramine. A particular detecting material is anti-rabbit antibody prepared in goats and conjugated with fluorescein through an isothiocyanate. Examples of preferred isotope include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. The radioactive label can be detected by any of the currently available counting procedures. While many enzymes can be used, examples of preferred enzymes are peroxidase, β-glucuronidase, β-D-glucosidase, β-D-galactosidase, urease, glucose oxidase plus peroxidase and alkaline phosphatase. Enzyme are conjugated to the selected particle by reaction with bridging molecules such as carbodiimides, diisocyanates, glutaraldehyde and the like. Enzyme labels can be detected by any of the presently utilized colorimetric, spectrophotometric, fluorospectrophotometric, amperometric or gasometric techniques. U.S. Pat. Nos. 3,654,090; 3,850,752; and 4,016,043 are referred to by way of example for their disclosure of alternate labelling material and methods.

The invention also provides a method of detecting antibodies to a polypeptide of the invention in biological samples, using the following steps: (a) providing a polypeptide of the invention or a fragment thereof; (b) incubating a biological sample with said polypeptide of the invention under conditions which allow for the formation of an antibody-antigen complex; and (c) determining whether an antibody-antigen complex with the polypeptide of the invention is formed.

In another embodiment of the invention there are provided in vitro methods for evaluating the level of antibodies to a polypeptide of the invention in a biological sample using the following steps: (a) detecting the formation of reaction complexes in a biological sample according to the method noted above; and (b) evaluating the amount of reaction complexes formed, which amount of reaction complexes corresponds to the level of polypeptide of the invention in the biological sample.

Further there are provided in vitro methods for monitoring therapeutic treatment of a disease associated with *B. hyodysenteriae* in an animal host by evaluating, as describe above, the levels of antibodies to a polypeptide of the invention in a series of biological samples obtained at different time points from an animal host undergoing such therapeutic treatment.

The present invention further provides methods for detecting the presence or absence of *B. hyodysenteriae* in a biological sample by: (a) bringing the biological sample into contact with a polynucleotide probe or primer of polynucleotide of the invention under suitable hybridizing conditions; and (b) detecting any duplex formed between the probe or primer and nucleic acid in the sample.

According to one embodiment of the invention, detection of *B. hyodysenteriae* may be accomplished by directly amplifying polynucleotide sequences from biological sample, using known techniques and then detecting the presence of polynucleotide of the invention sequences.

In one form of the invention, the target nucleic acid sequence is amplified by PCR and then detected using any of the specific methods mentioned above. Other useful diagnostic techniques for detecting the presence of polynucleotide sequences include, but are not limited to: 1) allele-specific PCR; 2) single stranded conformation analysis; 3) denaturing gradient gel electrophoresis; 4) RNase protection assays; 5) the use of proteins which recognize nucleotide mismatches, such as the *E. coli* mutS protein; 6) allele-specific oligonucleotides; and 7) fluorescent in situ hybridisation.

In addition to the above methods polynucleotide sequences may be detected using conventional probe technology. When probes are used to detect the presence of the desired polynucleotide sequences, the biological sample to be analysed, such as blood or serum, may be treated, if desired, to extract the nucleic acids. The sample polynucleotide sequences may be prepared in various ways to facilitate detection of the target sequence; e.g. denaturation, restriction digestion, electrophoresis or dot blotting. The targeted region of the sample polynucleotide sequence usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Sample polynucleotide sequences and probes are incubated under conditions that promote stable hybrid formation of the target sequence in the probe with the putative desired polynucleotide sequence in the sample. Preferably, high stringency conditions are used in order to prevent false positives.

Detection, if any, of the resulting hybrid is usually accomplished by the use of labelled probes. Alternatively, the probe may be unlabeled, but may be detectable by specific binding with a ligand that is labelled, either directly or indirectly. Suitable labels and methods for labelling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labelled moiety.

It is also contemplated within the scope of this invention that the nucleic acid probe assays of this invention may employ a cocktail of nucleic acid probes capable of detecting the desired polynucleotide sequences of this invention. Thus, in one example to detect the presence of polynucleotide sequences of this invention in a cell sample, more than one probe complementary to a polynucleotide sequences is employed and in particular the number of different probes is alternatively 2, 3, or 5 different nucleic acid probe sequences.

The polynucleotide sequences described herein (preferably in the form of probes) may also be immobilised to a solid phase support for the detection of *Brachyspira* species, including but not limited to *B. hyodysenteriae, B. intermedia, B. alvinipulli, B. aalborgi, B. innocens, B. murdochii,* and *B. pilosicoli.* Alternatively the polynucleotide sequences described herein will form part of a library of DNA molecules that may be used to detect simultaneously a number of different genes from *Brachyspira* species, such as *B. hyodysenteriae*. In a further alternate form of the invention polynucleotide sequences described herein together with other polynucleotide sequences (such as from other bacteria or viruses) may be immobilised on a solid support in such a manner permitting identification of the presence of a *Brachyspira* species, such as *B. hyodysenteriae* and/or any of the other polynucleotide sequences bound onto the solid support.

Techniques for producing immobilised libraries of DNA molecules have been described in the art. Generally, most prior art methods describe the synthesis of single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesize specific sets of probes at spatially defined locations on a substrate that may be used to produced the immobilised DNA libraries of the present invention. U.S. Pat. No. 5,837,832 also provides references for earlier techniques that may also be used. Thus polynucleotide sequence probes may be synthesised in situ on the surface of the substrate.

Alternatively, single-stranded molecules may be synthesised off the solid substrate and each pre-formed sequence applied to a discrete position on the solid substrate. For example, polynucleotide sequences may be printed directly onto the substrate using robotic devices equipped with either pins or pizo electric devices.

The library sequences are typically immobilised onto or in discrete regions of a solid substrate. The substrate may be porous to allow immobilisation within the substrate or substantially non-porous, in which case the library sequences are typically immobilised on the surface of the substrate. The solid substrate may be made of any material to which polypeptides can bind, either directly or indirectly. Examples of suitable solid substrates include flat glass, silicon wafers, mica, ceramics and organic polymers such as plastics, including polystyrene and polymethacrylate. It may also be possible to use semi-permeable membranes such as nitrocellulose or nylon membranes, which are widely available. The semi-permeable membranes may be mounted on a more robust solid surface such as glass. The surfaces may optionally be coated with a layer of metal, such as gold, platinum or other transition metal.

Preferably, the solid substrate is generally a material having a rigid or semi-rigid surface. In preferred embodiments, at least one surface of the substrate will be substantially flat, although in some embodiments it may be desirable to physically separate synthesis regions for different polymers with, for example, raised regions or etched trenches. It is also preferred that the solid substrate is suitable for the high density application of DNA sequences in discrete areas of typically from 50 to 100 µm, giving a density of 10000 to 40000 dots/cm$^{-2}$.

The solid substrate is conveniently divided up into sections. This may be achieved by techniques such as photoetching, or by the application of hydrophobic inks, for example teflon-based inks (Cel-line, USA).

Discrete positions, in which each different member of the library is located may have any convenient shape, e.g., circular, rectangular, elliptical, wedge-shaped, etc.

Attachment of the polynucleotide sequences to the substrate may be by covalent or non-covalent means. The polynucleotide sequences may be attached to the substrate via a layer of molecules to which the library sequences bind. For example, the polynucleotide sequences may be labelled with biotin and the substrate coated with avidin and/or streptavidin. A convenient feature of using biotinylated polynucleotide sequences is that the efficiency of coupling to the solid substrate can be determined easily. Since the polynucleotide sequences may bind only poorly to some solid substrates, it is often necessary to provide a chemical interface between the solid substrate (such as in the case of glass) and the nucleic acid sequences. Examples of suitable chemical interfaces include hexaethylene glycol. Another example is the use of polylysine coated glass, the polylysine then being chemically modified using standard procedures to introduce an affinity ligand. Other methods for attaching molecules to the surfaces of solid substrate by the use of coupling agents are known in the art, see for example WO98/49557.

Binding of complementary polynucleotide sequences to the immobilised nucleic acid library may be determined by a variety of means such as changes in the optical characteristics of the bound polynucleotide sequence (i.e. by the use of ethidium bromide) or by the use of labelled nucleic acids, such as polypeptides labelled with fluorophores. Other detection techniques that do not require the use of labels include optical techniques such as optoacoustics, reflectometry, ellipsometry and surface plasmon resonance (see WO97/49989).

Thus, the present invention provides a solid substrate having immobilized thereon at least one polynucleotide of the present invention, preferably two or more different polynucleotide sequences of the present invention.

The present invention also can be used as a prophylactic or therapeutic, which may be utilised for the purpose of stimulating humoral and cell mediated responses in animals, such as chickens and swine, thereby providing protection against colonisation with *Brachyspira* species, including but not limited to *B. hyodysenteriae, B. intermedia, B. alvinipulli, B. aalborgi, B. innocens, B. murdochii,* and *B. pilosicoli.* Natural infection with a *Brachyspira* species, such as *B. hyodysenteriae* induces circulating antibody titres against the proteins described herein. Therefore, the amino acid sequences described herein or parts thereof, have the potential to form the basis of a systemically or orally administered prophylactic or therapeutic to provide protection against intestinal spirochaetosis.

It is well appreciated by those skilled in the art there is a high degree of sequence conservation between species of *Brachyspira*. For example, as shown below *B. hyodysenteriae* outer membrane proteins (OMP) H122 and H114 have a high degree of similarity between a number of *Brachyspira* species.

Cross-species nucleotide similarity for *B. hyodysenteriae* OMP H114.

| *Brachyspira* species | Similarity at nucleotide level (%) H114 |
|---|---|
| *Brachyspira hyodysenteriae* | 100 |
| *Brachyspira pilosicoli* | 85.4 |
| *Brachyspira intermedia* | 93.9 |
| *Brachyspira murdochii* | 90.8 |
| *Brachyspira alvinpulli* | 93.8 |

Cross-species nucleotide similarity for *B. hyodysenteriae* OMP H122.

| *Brachyspira* species | Similarity at nucleotide level (%) H122 |
|---|---|
| *Brachyspira hyodysenteriae* | 100 |
| *Brachyspira pilosicoli* | 81.4 |
| *Brachyspira intermedia* | 87.5 |
| *Brachyspira murdochii* | 83.0 |
| *Brachyspira alvinipulli* | 82.9 |

Also as shown in Example 22, the nucleotide and amino acid sequences of the present invention are capable of producing cross-reactivity over a range of *Brachyspira* species not just *B. hyodysenteriae*. Accordingly, polypeptides used in the present invention are capable of use against other species of *Brachyspira* species not just *B. hyodysenteriae*.

Accordingly, in one embodiment the present invention provides the amino acid sequences described herein or fragments thereof or antibodies that bind the amino acid sequences or the polynucleotide sequences described herein in a therapeutically effective amount admixed with a pharmaceutically acceptable carrier, diluent, or excipient.

The phrase "therapeutically effective amount" is used herein to mean an amount sufficient to reduce by at least about 15%, preferably by at least 50%, more preferably by at least 90%, and most preferably prevent, a clinically significant deficit in the activity, function and response of the animal host. Alternatively, a therapeutically effective amount is sufficient to cause an improvement in a clinically significant condition in the animal host.

The phrase "pharmaceutically acceptable" refers to molecular entities and compositions that are physiologically tolerable and do not typically produce an allergic or similarly untoward reaction, such as gastric upset and the like, when administered to an animal. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or saline solutions and aqueous dextrose and glycerol solutions are preferably employed as carriers, particularly for injectable solutions. Suitable pharmaceutical carriers are described in Martin, *Remington's Pharmaceutical Sciences*, 18th Ed., Mack Publishing Co., Easton, Pa., (1990).

In a more specific form of the invention there are provided pharmaceutical compositions comprising therapeutically effective amounts of the amino acid sequences described herein or an analogue, fragment or derivative product thereof or antibodies thereto together with pharmaceutically acceptable diluents, preservatives, solubilizes, emulsifiers, adjuvants and/or carriers. Such compositions include diluents of various buffer content (e.g., Tris-HCl, acetate, phosphate), pH and ionic strength and additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol). The material may be incorporated into particulate preparations of polymeric compounds such as polylactic acid, polyglycolic acid, etc. or into liposomes. Hylauronic acid may also be used. Such compositions may influence the physical state, stability, rate of in vivo release, and rate of in vivo clearance of the present proteins and derivatives. See, e.g., Martin, *Remington's Pharmaceutical Sciences*, 18th Ed. (1990, Mack Publishing Co., Easton, Pa. 18042) pages 1435-1712 that are herein incorporated by reference. The compositions may be prepared in liquid form, or may be in dried powder, such as lyophilised form.

Alternatively, the polynucleotides of the invention can be optimized for expression in plants (e.g., corn). The plant may be transformed with plasmids containing the optimized polynucleotides. Then the plant is grown, and the proteins of the invention are expressed in the plant, or the plant-optimized version is expressed. The plant is later harvested, and the section of the plant containing the proteins of the invention is processed into feed for the animal. This animal feed will impart immunity against *B. hyodysenteriae* when eaten by the animal. Examples of prior art detailing these methods can be found in U.S. Pat. No. 5,914,123 (Arntzen, et al.); U.S. Pat. No. 6,034,298 (Lam, et al.); and U.S. Pat. No. 6,136,320 (Arntzen, et al.).

It will be appreciated that pharmaceutical compositions provided accordingly to the invention may be administered by any means known in the art. Preferably, the pharmaceutical compositions for administration are administered by injection, orally, or by the pulmonary, or nasal route. The amino acid sequences described herein or antibodies derived therefrom are more preferably delivered by intravenous, intraarterial, intraperitoneal, intramuscular, or subcutaneous routes of administration. Alternatively, the amino acid sequence described herein or antibodies derived therefrom, properly formulated, can be administered by nasal or oral administration.

In a specific embodiment of the invention, a vaccine composition may be a "combination vaccine" with one or more polynucleotide or polypeptide sequences of the invention which have a similar functional role that are combined in a vaccine. For example, the following three different functional groups can be combined as identified in the following tables:

Vaccine: 1

| Gene | Polynucleotide sequence SEQ ID No. | Polypeptide sequence SEQ ID No. |
|---|---|---|
| NAV-H77 | SEQ ID No. 1 | SEQ ID No. 2 |
| NAV-H105 | SEQ ID No. 3 | SEQ ID No. 4 |
| NAV-H109 | SEQ ID No. 5 | SEQ ID No. 6 |
| NAV-H114 | SEQ ID No. 7 | SEQ ID No. 8 |

Vaccine: 2

| Gene | Polynucleotide sequence SEQ ID No. | Polypeptide sequence SEQ ID No. |
|---|---|---|
| NAV-H116 | SEQ ID No. 9 | SEQ ID No. 10 |
| NAV-H122 | SEQ ID No. 11 | SEQ ID No. 12 |
| NAV-H147 | SEQ ID No. 13 | SEQ ID No. 14 |
| NAV-H155 | SEQ ID No. 15 | SEQ ID No. 16 |

Vaccine: 3

| Gene | Polynucleotide sequence SEQ ID No. | Polypeptide sequence SEQ ID No. |
|---|---|---|
| NAV-H161 | SEQ ID No. 17 | SEQ ID No. 18 |
| NAV-H173 | SEQ ID No. 19 | SEQ ID No. 20 |

A prerequisite for combination vaccines is a lack of competition (i.e. between antigens) and a high compatibility with respect to the subject to be immunized. According to international standard applied in connection with immunization, a combination vaccine should confer a protection which is comparable to that achieved by separate vaccinations. However, the combination of antigens is a complicated process which is associated with a number of problems and uncertainties.

As the individual components of a combination vaccine are not inert substances, the combination of various components into one mixture can negatively influence the immunogenicity of the individual antigenic components. For example, interactions between the different antigens or between the antigens and other components typically used in such vaccines can occur due to differences in charge, chemical residues, detergents, formaldehyde, concentration of ions etc. These changes can occur instantaneously after contacting the different antigens with each other or with other substances usually present in vaccine formulations. Moreover, these changes can also occur with a significant delay after mixing, for example during storage, shipping, etc. However, it cannot be predicted to which extent the immunogenicity of individual antigens may be influenced by mixing them to one combination. As a consequence, a situation can occur in which one or more antigens of the vaccine only confer an insufficient seroprotection against one or more of diseases which renders the product unsuitable for medical practice.

The production of effective combination vaccines is a complex matter which depends on multidimensional interactions between the individual components of the vaccine and does not allow to extrapolate any effect of the components observed when administered separately.

It has been found that the combination vaccines according to the present invention may be combined with one or more further antigens and remain effective and stable.

The term "stable" as used in the context of the present invention means that the combination vaccine formulation can be kept for a period of eight days or more preferably 14 days at room temperature without any substantial loss with respect to immunogenity and stability of its distinct antigen compounds. In order to enhance stability, stabilizing agents such as saccharose can be added to the vaccine composition. Instead of saccharose or in addition thereto, other stabilizers, e.g. human serum albumin, mannose, trehalose, mannite, or polygeline can also be added as stabilizing agents. The vaccines of the present invention exhibit a pH value of preferably between 5.0 to 8.0, more preferably between 6.0 to 7.0, wherein a pH value of 6.8 to 7.8 is most preferred.

The term "effective" as used herein, refers to the fact that the sequence of the invention upon single or repeated administration to a subject (for example, a mammal) confers protection against a specific disease.

As used herein the term "conferring protection" means that the sequence of the invention, upon administration, induces an immunological response in the vaccinated subject which response is capable to protect said subject from the symptoms of subsequent infection.

Also encompassed by the present invention is the use of polynucleotide sequences of the invention, as well as antisense and ribozyme polynucleotide sequences hybridisable to a polynucleotide sequence encoding an amino acid sequence according to the invention, for manufacture of a medicament for modulation of a disease associated *B. hyodysenteriae.*

Polynucleotide sequences encoding antisense constructs or ribozymes for use in therapeutic methods are desirably administered directly as a naked nucleic acid construct. Uptake of naked nucleic acid constructs by bacterial cells is enhanced by several known transfection techniques, for example those including the use of transfection agents. Example of these agents include cationic agents (for example calcium phosphate and DEAE-dextran) and lipofectants. Typically, nucleic acid constructs are mixed with the transfection agent to produce a composition.

Alternatively the antisense construct or ribozymes may be combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular, oral or transdermal administration. The routes of administration described are intended only as a guide since a skilled practitioner will be able to determine readily the optimum route of administration and any dosage for any particular animal and condition.

The invention also includes kits for screening animals suspected of being infected with a *Brachyspira* species, such as *B. hyodysenteriae* or to confirm that an animal is infected with a *Brachyspira* species, such as *B. hyodysenteriae*. In a further embodiment of this invention, kits suitable for use by a specialist may be prepared to determine the presence or absence of *Brachyspira* species, including but not limited to *B. hyodysenteriae, B. intermedia, B. alvinipulli, B. aalborgi, B. innocens, B. murdochii*, and *B. pilosicoli* in suspected infected animals or to quantitatively measure a *Brachyspira* species, including but not limited to *B. hyodysenteriae, B. intermedia, B. alvinipulli, B. aalborgi* and *B. pilosicoli* infection. In accordance with the testing techniques discussed above, such kits can contain at least a labelled version of one of the amino acid sequences described herein or its binding partner, for instance an antibody specific thereto, and directions depending upon the method selected, e.g., "competitive," "sandwich," "DASP" and the like. Alternatively, such kits can contain at least a polynucleotide sequence complementary to a portion of one of the polynucleotide sequences described herein together with instructions for its use. The kits may also contain peripheral reagents such as buffers, stabilizers, etc.

Accordingly, a test kit for the demonstration of the presence of a *Brachyspira* species, including but not limited to *B. hyodysenteriae, B. intermedia, B. alvinipulli, B. aalborgi, B. innocens, B. murdochii*, and *B. pilosicoli*, may contain the following:

(a) a predetermined amount of at least one labelled immunochemically reactive component obtained by the direct or indirect attachment of one of the amino acid sequences described herein or a specific binding partner thereto, to a detectable label;

(b) other reagents; and (c) directions for use of said kit.

More specifically, the diagnostic test kit may contain:

(a) a known amount of one of the amino acid sequences described herein as described above (or a binding partner) generally bound to a solid phase to form an immunosorbent, or in the alternative, bound to a suitable tag, or there are a plural of such end products, etc;

(b) if necessary, other reagents; and (c) directions for use of said test kit.

In a further variation, the test kit may contain:

(a) a labelled component which has been obtained by coupling one of the amino acid sequences described herein to a detectable label;

(b) one or more additional immunochemical reagents of which at least one reagent is a ligand or an immobilized ligand, which ligand is selected from the group consisting of:

(i) a ligand capable of binding with the labelled component (a);

(ii) a ligand capable of binding with a binding partner of the labelled component (a);

(iii) a ligand capable of binding with at least one of the component(s) to be determined; or (iv) a ligand capable of binding with at least one of the binding partners of at least one of the component(s) to be determined; and (c) directions for the performance of a protocol for the detection and/or determination, of one or more components of an immunochemical reaction between one of the amino acid sequences described herein and a specific binding partner thereto.

In one embodiment, the present invention provides simple point-of-care kit that uses principles similar to the widely-used serum testing kits, for the rapid detection of the circulating antibodies in the animal to the polypeptides of the invention will allow the healthcare professional or veterinarian to rapidly diagnose *Brachyspira* infection, and to rapidly institute proven and effective therapeutic and preventive measures. The use of the kit can represent the standard of care for all animals that are at risk of developing *Brachyspira* infection.

The methods and kits of the present invention can also provide a means for detecting or monitoring *Brachyspira* infection including the change in status. It can be especially useful in detecting early stage *Brachyspira* infection. Thus, the invention also provides a means for a healthcare professional or veterinarian to monitor the progression of *Brachyspira* infection (worsening, improving, or remaining the same) during and following treatment. Typically, the healthcare professional or veterinarian would establish a protocol of collecting and analysing a quantity of biological sample from the animal at selected intervals. Typically the sample is obtained intermittently during a prescribed period. The period of time between intermittent sampling may be dictated by the condition of the animal, and can range from a sample each 24 hours to a sample taken days, weeks or even months apart.

A point-of-care kit for use in the method typically comprises a media having affixed thereto one or more capture polypeptides, whereby the sample is contacted with the media to expose the capture polypeptides to the circulating antibodies contained in the sample. The kit includes an acquiring means that can comprise an implement, such as a needle or vacutainer, having a surface comprising the media. The acquiring means can also comprise a container for accepting the sample, where the container has a serum-contacting surface that comprises the media. In another typical embodiment, the assay for detecting the complex of the circulating antibodies and the capture polypeptides can comprise an ELISA, and can be used to quantitate the amount of circulating antibodies to the polypeptides of the invention in a sample. In an alternative embodiment, the acquiring means can comprise an implement comprising a cassette containing the media.

A method and kit of the present invention for detecting the circulating antibodies to the polypeptides of the invention can be made by adapting the methods and kits known in the art for the rapid detection of other proteins and ligands in a biological sample. Examples of methods and kits that can be adapted to the present invention are described in U.S. Pat. No. 5,656,503, issued to May et al. on Aug. 12, 1997, U.S. Pat. No. 6,500,627, issued to O'Conner et al. on Dec. 31, 2002, U.S. Pat. No. 4,870,007, issued to Smith-Lewis on Sep. 26, 1989, U.S. Pat. No. 5,273,743, issued to Ahlem et al. on Dec. 28, 1993, and U.S. Pat. No. 4,632,901, issued to Valkers et al. on Dec. 30, 1986, all such references being hereby incorporated by reference.

A rapid one-step method of detecting the circulating antibodies to the polypeptides of the present invention can reduce the time for detecting the development of *Brachyspira* infection. A typical method can comprise the steps of: obtaining a sample from an animal at risk of or suspected of having a *Brachyspira* infection; mixing a portion of the sample with one or more detecting polypeptides which specifically bind to one of the circulating antibodies, so as to initiate the binding of the detecting polypeptides to the circulating antibodies in the sample; contacting the mixture of sample and detecting polypeptides with an immobilized capture antibody which specifically binds to the detecting polypeptides, which capture antibody does not cross-react with the detecting polypeptide, so as to bind the detecting polypeptide to the circulating antibodies, and the circulating antibodies to the capture antibody, to form a detectable complex; removing unbound detecting polypeptide and any unbound sample from the complex; and detecting the detecting polypeptide of the complex. The detectable polypeptide can be labelled with a detectable marker, such as a radioactive label, enzyme, biological dye, magnetic bead, or biotin, as is well known in the art.

The following examples are provided for the purposes of illustration and are not intended to limit the scope of the invention.

Example 1

Genome Sequencing

An Australian porcine field isolate of *B. hyodysenteriae* (strain WA1) is shotgun sequenced. This strain has been well-characterised and shown to be virulent following experimental challenge of pigs. The spirochaete is grown in anaerobic trypticase soy broth culture and 100 μg DNA was extracted using a cetyltrimethylammonium bromide (CTAB) method to prepare high quality chromosomal DNA suitable for preparation of genomic DNA libraries. The genomic DNA is sheared using a GeneMachines Hydroshear, and the fragmented DNA processed for cloning as per the protocol recommended by the suppliers of the pSMART vector system (Lucigen). A small insert (2-3 kb) library and a medium insert (3-10 kb) library are constructed into the low copy version of the pSMART vector.

Example 2

Annotation

Partial genome sequences for *B. hyodysenteriae* are assembled and annotated by the Australian Genome Research Facility (AGRF) in Queensland and at Murdoch University by the Centre for Bioinformatics and Biological Computing (CBBC). The CBBC uses up-to-date mirrors of the major international databases and have developed leading edge bioinformatics software and strategies for annotation of features in large genome sequences. A range of public domain bioinformatics tools are used to analyse and re-analyse the sequences as part of a quality assurance procedure on data analysis. Open reading frames (ORFs) are predicted using a variety of programs including GeneMark, GLIMMER, ORPHEUS, SELFID and GetORF. Putative ORFs are examined for homology (DNA and protein) with existing international databases using searches including BLAST and FASTA. All the predicted ORFs are analysed to determine their cellular localisation using programs such as PSI-BLAST, FASTA, MOTIFS, FINDPATTERNS, PHD, SIGNALP and PSORT. Databases including Interpro, Prosite, Propom, Pfam and Blocks are used to predict surface associated proteins such as transmembrane domains, leader peptides, homologies to know surface proteins, lipoprotein signature, outer membrane anchoring motifs and host cell binding domains. Phylogenetic and other molecular evolution analysis is conducted with the identified genes and with other species to assist in the assignment of function. The in silico analysis of both partially sequenced genomes has produced a comprehensive list of all the predicted ORFs present in the sequence data available. Each ORF is interrogated for descriptive information such as predicted molecular weight, isoelectric point, hydrophobicity, and subcellular localisation to enable correlation with the in vitro properties of the native gene product. Predicted genes which encode proteins similar to surface localized components and virulence factors in other pathogenic bacteria are selected as potential vaccine targets.

Example 3

Analysis of Gene Distribution Using PCR

One or two primer pairs which anneal to different regions of the target gene coding region are designed and optimised for PCR detection. Distribution analysis of the *B. hyodysenteriae* target genes is performed on 23 strains of *B. hyodysenteriae*, including two strains which have been shown to be avirulent. Primer sets used in the distribution analysis are shown in Table 1. PCR analysis is performed in a 25 µl total volume using Taq DNA polymerase. The amplification mixture consisted of 1×PCR buffer (containing 1.5 mM of MgCl2), 1 U of Taq DNA polymerase, 0.2 mM of each dNTP, 0.5 µM of the primer pair, and 1 µl purified chromosomal template DNA. Cycling conditions involved an initial template denaturation step of 5 min at 94° C., followed by 30 cycles of denaturation at 94° C. for 30 s, annealing at 50° C. for 15 s, and primer extension at 72° C. for 1 min. The PCR products are subjected to electrophoresis in 1% (w/v) agarose gels in 1×TAE buffer (40 mM Tris-acetate, 1 mM EDTA), stained with a 1 µg/ml ethidium bromide solution and viewed over ultraviolet (UV) light.

TABLE 1

OLIGONUCLEOTIDE PRIMERS USED IN THE DISTRIBUTION ANALYSIS OF THE *B. HYODYSENTERIAE* VACCINE CANDIDATE GENES

| Gene | Primer name | Primer Sequence (5'-3') | SEQ ID No. |
|---|---|---|---|
| NAV-H77 | H77-F26 | GCTTATTTACTATGGTGTCGGCATTAG | SEQ ID No. 21 |
| | H77-R696 | ATATCTTTCTTCTTCTTCGTCTTCTTC | SEQ ID No. 22 |
| NAV-H105 | H105-F286 | AGAATACCTCTTTCACGCGGACTTGGA | SEQ ID No. 23 |
| | H105-R456 | ACCTCCCAATATTGCAGGAG | SEQ ID No. 24 |
| NAV-H109 | H109-F64 | TTTGTTATGGGCTTTGTAGG | SEQ ID No. 25 |
| | H109-R513 | AAGAAGAAAATCTGCTGAAAC | SEQ ID No. 26 |
| NAV-H114 | H114-F46 | ATTCAATGCGGTAATAAAACAGATAC | SEQ ID No. 27 |
| | H114-R650 | ATGCTAATATCCCCTACTTCTTCAAG | SEQ ID No. 28 |
| NAV-H116 | H116-F210 | TGAATCGGCTGTAAAGCAGGCA | SEQ ID No. 29 |
| | H116-R266 | ACACCCGCATCAAATCCAGCACCTGA | SEQ ID No. 30 |
| NAV-H122 | H122-F54 | TCTTATGGCTAAAAGCGGATTCGGA | SEQ ID No. 31 |
| | H122-R385 | GAGGGAATTTTACACCTGCTCCAACACC | SEQ ID No. 32 |
| NAV-H147 | H147-F185 | TCGCTGAAGGTTATGCATCTGC | SEQ ID No. 33 |
| | H147-R489 | TCTGTCCATCAGTATGCCCATTGCCTGA | SEQ ID No. 34 |
| NAV-H155 | H155-F64 | CAATTTGATGCTAGCATATATGCAC | SEQ ID No. 35 |
| | H155-R760 | AATTTAAAGCAATTTCTAAACTGCTAAATC | SEQ ID No. 36 |
| NAV-H161 | H161-F124 | AGCAGATCATACTCTATAAAAACAGG | SEQ ID No. 37 |
| | H161-R586 | GTCTATTAGCAAATAAGAACTCCAATG | SEQ ID No. 38 |
| NAV-H173 | H173-F272 | TAAAAGGAGAAAAAGGAAGATACG | SEQ ID No. 39 |
| | H179-R705 | ATTATCTTGATGAGGATGCTTTC | SEQ ID No. 40 |

Example 4

Bioinformatics

Shot-gun sequencing of the *B. hyodysenteriae* genome resulted in 73% (2,347.8 kb out of a predicted 2,300 kb) of the genome to be sequenced. These sequences are comprised of 171 contigs with an average contig size of 13.7 kb. From the 171 contigs, 1,860 open-reading frames (ORFs) are predicted. Comparison of the predicted ORFs with genes present in the nucleic acid and protein databases indicated that approximately 70% in each species have homology with genes contained in the databases. The remaining 30% of the predicted ORFs from each genome have no known identity.

Example 5

Vaccine Candidates

The gene products of the predicted ORFs were analysed using the PSORTb Subcellular Localisation Prediction Tool (Gardy, J. L., Laird, M. R., Chen, F., Rey, S., Walsh, C. J., Ester, M. and Brinkman, F. S. L. (2005) PSORTb v.2.0: expanded prediction of bacterial protein subcellular localization and insights gained from comparative proteome analysis. Bioinformatics 21:617-623.] to determine the probable subcellular localisation of the protein. Proteins with a significant probability of having an extracellular or outer membrane localisation were selected as potential candidate antigens for vaccine and serology. Table 2 provides the basic descriptive information associated with each selected gene and its putative gene product.

TABLE 2

DESCRIPTIVE INFORMATION ASSOCIATED WITH THE *B. HYODYSENTERIAE* GENES AND PUTATIVE GENE PRODUCTS PREDICTED BY PSORTB TO HAVE AN OUTER MEMBRANE LOCALISATION

| Gene | SEQ ID Nos. | Gene size (bp) | Protein size (aa) | Predicted MW (Da) | Predicted pI |
| --- | --- | --- | --- | --- | --- |
| NAV-H77 | Nucleotide seq. SEQ ID No. 1<br>Amino acid seq. SEQ ID No. 2 | 702 | 234 | 27,291 | 4.8096 |
| NAV-H105 | Nucleotide seq. SEQ ID No. 3<br>Amino acid seq. SEQ ID No. 4 | 942 | 314 | 35,447 | 9.9264 |
| NAV-H109 | Nucleotide seq. SEQ ID No. 5<br>Amino acid seq. SEQ ID No. 6 | 675 | 225 | 26,275 | 5.3190 |
| NAV-H114 | Nucleotide seq. SEQ ID No. 7<br>Amino acid seq. SEQ ID No. 8 | 996 | 332 | 39,199 | 4.0603 |
| NAV-H116 | Nucleotide seq. SEQ ID No. 9<br>Amino acid seq. SEQ ID No. 10 | 810 | 270 | 29,654 | 9.9131 |
| NAV-H122 | Nucleotide seq. SEQ ID No. 11<br>Amino acid seq. SEQ ID No. 12 | 639 | 213 | 24,082 | 5.2678 |
| NAV-H147 | Nucleotide seq. SEQ ID No. 13<br>Amino acid seq. SEQ ID No. 14 | 1239 | 413 | 45,175 | 7.4703 |
| NAV-H155 | Nucleotide seq. SEQ ID No. 15<br>Amino acid seq. SEQ ID No. 16 | 759 | 253 | 28,879 | 5.2134 |
| NAV-H161 | Nucleotide seq. SEQ ID No. 17<br>Amino acid seq. SEQ ID No. 18 | 792 | 264 | 32,298 | 4.6577 |
| NAV-H173 | Nucleotide seq. SEQ ID No. 19<br>Amino acid seq. SEQ ID No. 20 | 639 | 213 | 23,789 | 8.3429 |

Example 6

Gene Distribution

The overall gene distribution of each ORF is summarized in Table 3. A total of 23 *B. hyodysenteriae* strains are analysed. The distribution is determined from the cumulative result of PCR using up to two different primer sets. All of the ORFS are present in 91-100% of the *B. hyodysenteriae* strains tested.

TABLE 3

GENE DISTRIBUTION OF THE *B. hyodysenteriae* VACCINE CANDIDATES ANALYSED BY PCR USING A PANEL OF 23 DIFFERENT STRAINS

| Gene | Distribution (%) |
| --- | --- |
| NAV-H77 | 96 |
| NAV-H105 | 91 |
| NAV-H109 | 100 |
| NAV-H114 | 100 |
| NAV-H116 | 91 |
| NAV-H122 | 91 |
| NAV-H147 | 100 |
| NAV-H155 | 100 |
| NAV-H161 | 100 |
| NAV-H173 | 100 |

Example 7

Plasmid Extraction

*Escherichia coli* JM109 clones harbouring the pET-19b plasmid (Novagen) are streaked out from glycerol stock storage onto Luria-Bertani (LB) agar plates supplemented with 100 mg/l ampicillin and incubated at 37° C. for 16 h. A single colony is used to inoculate 10 ml of LB broth supplemented with 100 mg/l ampicillin and the broth culture was incubated at 37° C. for 12 h with shaking. The entire overnight culture is centrifuged at 5,000×g for 10 min and the plasmid contained in the cells extracted using the QIAprep Spin Miniprep Kit (Qiagen) according to the manufacturer's instructions. The purified plasmid is quantified using a fluorometer and the DNA concentration adjusted to 100 μg/ml by dilution with TE (10 mM Tris-HCl, 1 mM EDTA, pH 8.0) buffer. The purified pET-19b plasmid is stored at −20° C.

Example 8

Vector Preparation

Two µg of the purified pET-19b plasmid is digested at 37° C. for 1-4 h in a total volume of 50 µl containing 50 mM Tris-HCl (pH 7.5), 100 mM NaCl, 10 mM MgCl$_2$, 0.1 mg/ml bovine serum albumin (BSA) and 5 U of NdeI and BamHT (Fermentas). The linearised vectors are verified by electrophoresing 1 µl of the digestion reaction through a 1% (w/v) agarose gel in 1×TAE buffer at 90V for 1 h. The electrophoresed DNA is stained with 1 µg/ml ethidium bromide and viewed over UV light.

Linearised pET-19b vectors are purified using the Ultra-Clean PCR Clean-up Kit (Mo Bio Laboratories) according to the manufacturer's instructions. The purified linear vectors are quantified using the NanoDrop ND1000 spectrophotometer and the DNA concentration adjusted to 50 µg/ml by dilution with TE buffer. The linearised vectors are stored at −20° C.

Example 9

Insert Preparation—Primer Design

Primer pairs are designed to amplify as much of the coding region of the target gene as possible. All primers sequences include terminal restriction enzyme recognition sites to enable cohesive-end ligation of the resultant amplicon into the linearised pET-19b vector. The primer sequences used for cloning are shown in Table 4. The primers are tested using Amplify 3.0 (University of Wisconsin) and the theoretical amplicon sequence is inserted into the appropriate position in the pET-19b vector sequence. Deduced translation of the chimeric pET-19b expression cassette is performed using Vector NTI Advance version 10 (Invitrogen) to confirm that the gene inserts would be in the correct reading frame.

TABLE 4

OLIGONUCLEOTIDE PRIMERS USED IN THE CLONING OF THE B. hyodysenteriae GENES INTO THE PET-19B VECTOR. THE APPARENT MOLECULAR WEIGHT IS DETERMINED FROM SDS-PAGE

| Gene | Primer name | Primer Sequence (5'-3') | Predicted MW of native protein (Da) | Apparent MW of recombinant protein (kDa) |
|---|---|---|---|---|
| NAV-H77 | H77-F-NdeI | ATTACATATGTCTCATGCTTTAGGTGTAGGACTTTATATC (SEQ ID No. 41) | 27,291 | 26.6 |
|  | H77-R-BamHI | AATTGGATCCATATAAATATCTTTCTTCTTCTTCGTC (SEQ ID No. 42) |  |  |
| NAV-H105 | H105-F-NdeI | AACTCATATGATACCTGCTACATCTGCGAATATTG (SEQ ID No. 43) | 35,447 | 49.9 |
|  | H105-R-BamHI | TTTTGGATCCACACCTTTTTGAGGTATATTTAAAAC (SEQ ID No. 44) |  |  |
| NAV-H109 | H109-F-NdeI | TCTTCATATGGCTGACTTTGTTATGGGCTTTGTAGGAAG (SEQ ID No. 45) | 26,275 | 28.4 |
|  | H109-R-BamHI | TCTAGGATCCAAATACATACCCATTTGGAAACCTATATC (SEQ ID No. 46) |  |  |
| NAV-H114 | H114-F-NdeI | TATACATATGTGCGGTAATAAAACAGATACTCAAACTAC (SEQ ID No. 47) | 39,199 | 55.4 |
|  | H114-R-BamHI | ATTAGGATCCTTTTTAAAAACTCCGCTGAATCCATAG (SEQ ID No. 48) |  |  |
| NAV-H116 | H116-F-NdeI | TGTTCATATGAAAAGCGGTATTGAGATAGGTATATTTGTTC (SEQ ID No. 49) | 29,654 | 32.1 |
|  | H116-R-BamHI | GGAAGGATCCTAACACCTATTTGGAAACCTATATC (SEQ ID No. 50) |  |  |
| NAV-H122 | H122-F-NdeI | TCTTCATATGAAAAGCGGATTCGGAGTTGATTTAAC (SEQ ID No. 51) | 24,082 | 26.8 |
|  | H122-R-BamHI | GAATGGATCCCCTATTTGACCGCCTATATCAAATC (SEQ ID No. 52) |  |  |
| NAV-H147 | H147-F-NdeI | TTTTCATATGTGTGCTACAACTTCTAAAAGTACATC (SEQ ID No. 53) | 45,175 | 57.9 |
|  | H147-R-BamHI | CCTCGGATCCGCCTTTAAAGTAATAGTTTTATCATC (SEQ ID No. 54) |  |  |

TABLE 4-continued

OLIGONUCLEOTIDE PRIMERS USED IN THE CLONING OF THE *B. hyodysenteriae* GENES INTO THE PET-19B VECTOR. THE APPARENT MOLECULAR WEIGHT IS DETERMINED FROM SDS-PAGE

| Gene | Primer name | Primer Sequence (5'-3') | Predicted MW of native protein (Da) | Apparent MW of recombinant protein (kDa) |
|---|---|---|---|---|
| NAV-H155 | H155-F-NdeI | ATTACATATGCAATTTGATGCTAGCATATATGCAC (SEQ ID No. 55) | 28,879 | 30.3 |
| | H155-R-BamHI | TTTAGGATCCAATTTAAAGCAATTTCTAAACTGCTAAATC (SEQ ID No. 56) | | |
| NAV-H161 | H161-F-NdeI | TAAACATATGGTAAGAGATAAATATTCAGAAGAG (SEQ ID No. 57) | 32,298 | 33.0 |
| | H161-R-BamHI | TATTGGATCCCCTCTTTTATAGCTTATAGAAGCCTTAAC (SEQ ID No. 58) | | |
| NAV-H173 | H173-F-NdeI | TTTGCATATGAAAACAGGATTTGAGGTTAATGTATTATTTC (SEQ ID No. 59) | 23,789 | 26.8 |
| | H173-R-BamHI | AAATGGATCCCCAATCTGAGCACCTAAATCAACACTTG (SEQ ID No. 60) | | |

Example 10

Amplification of the Gene Inserts

All target gene inserts are amplified by PCR in a 100 µl total volume using Taq DNA polymerase and Pfu DNA polymerase. Briefly, the amplification mixture consists of PCR buffer (containing 1.5 mM of $MgCl_2$), 2 U of Taq DNA polymerase, 0.01 U Pfu DNA polymerase, 0.2 mM of each dNTP, 0.5 µM of the appropriate primer pair and 1 µl of purified chromosomal DNA. The chromosomal DNA is prepared from the same *B. hyodysenteriae* strain used for genome sequencing. Cycling conditions involve an initial template denaturation step of 5 min at 94° C., followed by 30 cycles of denaturation at 94° C. for 30 s, annealing at 50° C. for 15 s, and primer extension at 72° C. for 1 min. The PCR products are subjected to electrophoresis in 1% (w/v) agarose gels in 1×TAE buffer, stained with a 1 μg/ml ethidium bromide solution and viewed over UV light. After verifying the presence of the correct size PCR product, the PCR reaction is purified using the UltraClean PCR Clean-up Kit (Mo Bio Laboratories).

Example 11

Restriction Enzyme Digestion of the Gene Inserts

Thirty μl of the purified PCR product is digested in a 50 μl total volume with 1 U of NdeI and 1 U of BamHI. The digested insert DNA are purified using the UltraClean PCR Clean-up Kit (Mo Bio Laboratories). Purified digested insert DNA are quantified using the NanoDrop ND1000 spectrophotemeter and the DNA concentration adjusted to 10 μg/ml by dilution with TE buffer. The purified restricted insert DNA are used immediately for vector ligation.

Example 12

Ligation of the Gene Inserts into the pET-19b Vector

Ligation reactions are all performed in a total volume of 20 μl. Twenty five ng of linearised pTrcHis is incubated with an equi-molar amount of restricted insert at 16° C. for 16 h in 30 mM Tris-HCl (pH 7.8), 10 mM MgCl2, 10 mM DTT and 1 mM ATP containing 1 U of T4 DNA ligase (Fermentas). An identical ligation reaction containing no insert DNA is also included as a vector re-circularisation negative control.

Example 13

Transformation of pET-19b Ligations into *E. Coli* JM109 Cells

Competent *E. coli* JM109 cells are thawed from −80° C. storage on ice and then 50 μl of the cells are transferred into ice-cold 1.5 ml microfuge tubes containing 5 μl of the overnight ligation reactions. The tubes are mixed by gently tapping the bottom of each tube on the bench and left on ice for 30 min. The cells are then heat-shocked by placing the tubes into a 42° C. waterbath for 45 s before returning the tube to ice for 2 min. The transformed cells are recovered in 1 ml LB broth for 1 h at 37° C. with gentle mixing. The recovered cells are harvested at 2,500×g for 5 min and the cells resuspended in 50 μl of fresh LB broth. The entire 50 μl of resuspended cells are spread evenly onto a LB agar plate containing 100 mg/l ampicillin using a sterile glass rod. Plates are incubated at 37° C. for 16 h.

Example 14

Detection of Recombinant pET-19b Constructs in *E. Coli* by PCR

Twelve single transformant colonies for each construct are streaked onto fresh LB agar plates containing 100 mg/l ampicillin and incubated at 37° C. for 16 h. A single colony from each transformation event is resuspended in 50 μl of TE buffer and boiled for 1 min. Two μl of boiled cells are used as template for PCR. The amplification mixture consists of 1×PCR buffer (containing 1.5 mM of $MgCl_2$), 1 U of Taq DNA polymerase, 0.2 mM of each dNTP, 0.5 μM of the pET-19b-F primer (5'-GGAATTGTGAGCGGATAAC-3') and 0.5 µM of the pET-19b-R primer (5'-GCAAAAAAC-CCCTCAAGAC-3'). Cycling conditions involve an initial template denaturation step of 5 min at 94° C., followed by 30 cycles of denaturation at 94° C. for 30 s, annealing at 60° C. for 15 s, and a primer extension at 72° C. for 1 min. The PCR products are subjected to electrophoresis in 1% (w/v) agarose gels in 1×TAE buffer, stained with a 1 µg/ml ethidium bromide solution and viewed over UV light.

Example 15

Purification of Recombinant pET-19b Plasmids

An $E.$ $coli$ JM109 clone harbouring the successfully ligated pET-19b plasmids are inoculated into 5 ml of LB broth supplemented with 100 mg/l ampicillin and the broth culture is incubated at 37° C. for 12 h with shaking. The entire overnight culture is centrifuged at 5,000×g for 10 min and the plasmid contained in the cells extracted using the QIAprep Spin Miniprep Kit (Qiagen) according to the manufacturer's instructions. The purified recombinant pET-19b plasmid is stored at −20° C.

Example 16

Transformation of Recombinant pET-19b Plasmids into $E.$ $coli$ BL21 (DE3) Cells Competent $E.$ $coli$ BL21 (DE3) cells are thawed from −80° C. storage on ice and then 20 µl of the cells are transferred into ice-cold 1.5 ml microfuge tubes containing 1 µl of the recombinant purified pET-19b plasmid. The tubes are mixed by gently tapping the bottom of each tube on the bench and left on ice for 30 min. The cells are then heat-shocked by placing the tubes into a 42° C. waterbath for 45 s before returning the tube to ice for 2 min. The transformed cells are recovered in 1 ml LB broth for 1 h at 37° C. with gentle mixing. Fifty µl of the recovered cells are spread evenly onto a LB agar plate containing 100 mg/l ampicillin using a sterile glass rod. Plates are incubated at 37° C. for 16 h.

Example 17

Expression of Recombinant His-Tagged Proteins

Four isolated colonies of recombinant pET-19b plasmid in $E.$ $coli$ BL21 (DE3) is inoculated into 3 ml LB broth in a 10 ml centrifuge tube containing 100 mg/l ampicillin and 1 mM IPTG and incubated at 37° C. for 16 h with shaking. The cells are harvested by centrifugation at 5,000×g for 10 min at 4° C. The supernatant is discarded and each pellet is resuspended with 300 µl of 1×SDS-PAGE loading buffer (250 mM Tris-HCl pH 6.0, 8% w/v SDS, 200 mM DTT, 40% v/v glycerol and 0.04% w/v bromophenol blue). After boiling the tube for 5 min, the cellular debris is pelleted by centrifugation at 10,000×g for 10 min at 4° C. The supernatant is transferred to a new tube and stored at −20° C. until analysis.

Example 18

SDS-PAGE

SDS-PAGE analysis of protein involved electrophoretic separation using a discontinuous Tris-glycine buffer system. Ten µl of the prepared cell lysate is loaded into the wells of a polyacrylamide gel. The gel is comprised of a stacking gel (125 mM Tris-HCl ph 6.8, 4% w/v acylamide, 0.15% w/v bis-acrylamide and 0.1% w/v SDS) and a separating gel (375 mM Tris-HCl ph 8.8, 12% w/v acylamide, 0.31% w/v bis-acrylamide and 0.1% w/v SDS). These gels are polymerised by the addition of 0.1% (v/v) TEMED and 0.05% (w/v) freshly prepared ammonium sulphate solution and cast into the mini-Protean dual slab cell (Bio-Rad). Samples are run at 150 V at room temperature (RT) until the bromophenol blue dye-front reached the bottom of the gel. Pre-stained molecular weight standards are electrophoresed in parallel with the samples in order to allow molecular weight estimations. After electrophoresis, the gel is immediately stained using Coomassie Brilliant Blue G250 or subjected to electro-transfer onto nitrocellulose membrane for Western blotting.

Example 19

Western Blot Analysis

Electrophoretic transfer of separated proteins from the SDS-PAGE gel to nitrocellulose membrane is performed using the Towbin transfer buffer system. After electrophoresis, the gel is equilibrated in transfer buffer (25 mM Tris, 192 mM glycine, 20% v/v methanol, pH 8.3) for 15 min. The proteins in the gel are transferred to nitrocellulose membrane using the mini-Protean transblot apparatus (Bio-Rad). After assembly of the gel holder according to the manufacturer's instructions, electrophoretic transfer is performed at 30 V overnight at 4° C. The freshly transferred nitrocellulose membrane containing the separated proteins is blocked with 10 ml of tris-buffered saline (TBS; 20 mM Tris-HCl, 500 mM NaCl, pH 7.5) containing 5% (w/v) skim milk powder for 1 h at RT. The membrane is washed with TBS containing 0.1% (v/v) Tween 20 (TBST) and then incubated with 10 ml mouse anti-his antibody (diluted 5,000-fold with TBST) for 1 h at RT. After washing three times for 5 min with TBST, the membrane is incubated with 10 mL goat anti-mouse IgG (whole molecule)-AP diluted 5,000-fold in TBST for 1 h at RT. The membrane is developed using the Alkaline Phosphatase Substrate Kit (Bio-Rad). The development reaction is stopped by washing the membrane with distilled water. The membrane is then dried and scanned for presentation.

Example 20

Expression and Purification of Recombinant His-Tagged Proteins

A single colony of the recombinant pET-19b plasmid in $E.$ $coli$ BL21 (DE3) is inoculated into 20 ml LB broth in a 50 ml centrifuge tube containing 100 mg/l ampicillin and incubated at 37 C for 16 h with shaking. A 2 l conical flask containing 500 ml of LB broth supplemented with 100 mg/l ampicillin is inoculated with 10 ml of the overnight culture and incubated at 37° C. until the optical density of the cells at 600 nm is 0.5 (approximately 3-4 h). The culture is then induced by adding IPTG to a final concentration of 1 mM and the cells returned to 37° C. with shaking. After 6 h of induction, the culture is transferred to two 250 ml centrifuge bottles and the bottles are centrifuged at 5,000×g for 10 min at 25° C. The supernatant is discarded and each pellet is resuspended with 4 ml of Ni-NTA native lysis buffer (50 mM $NaH_2PO_4$, 300 mM NaCl, 10 mM imidazole, pH 8.0). The resuspended cells are pooled and stored at −20° C. overnight.

The cell suspension is removed from −20° C. storage and thawed on ice. Five µl of DNAse I (10 mg/ml) is added to the thawed lysate and incubated on ice for 1 h. The lysate is centrifuged at 20,000×g for 15 min at 4° C. The supernatant is transferred to a 10 ml column containing a 1 ml bed volume of Ni-NTA agarose resin (Qiagen). The recombinant his-tagged protein is allowed to bind to the resin for 1 h at 4° C. with end-over-end mixing. The resin is then ished with 30 ml of Ni-NTA native ish buffer (50 mM $NaH_2PO_4$, 300 mM NaCl, 20 mM imidazole, pH 8.0) before elution with 9 ml of Ni-NTA native elution buffer (50 mM $NaH_2PO_4$, 300 mM NaCl, 250 mM imidazole, pH 8.0). Three 3 ml fractions of the eluate are collected and stored at 4° C. Thirty µl of each eluate is treated with 10 µl of 4× sample treatment buffer and boiled for 5 min. The samples are subjected to SDS-PAGE and stained with Coomassie Brilliant Blue G250. The stained gel is equilibrated in distilled water for 1 h and dried between two sheets of cellulose overnight at RT.

Example 21

Dialysis and Lyophilisation of the Purified Recombinant His-Tagged Protein

The eluted proteins are pooled and transferred into a hydrated dialysis tube with a molecular weight cut-off (MWCO) of 3,500 Da. A 200 µl aliquot of the pooled eluate is taken and quantified using a commercial Protein Assay (Bio-Rad). The proteins are dialysed against 2 l of distilled water at 4° C. with stirring. The dialysis buffer is changed 8 times at 12-hourly intervals. The dialysed proteins are transferred from the dialysis tube into a 50 ml centrifuge tubes (40 ml maximum volume) and the tubes are placed at −80° C. overnight. Tubes are placed into a freeze-drier and lyophilised to dryness. The lyophilised proteins are then re-hydrated with PBS to a calculated concentration of 2 mg/ml and stored at −20° C.

Example 22

Serology Using Recombinant Protein

Ten µg of purified recombinant protein is diluted in 10 ml of carbonate buffer and 100 µl is added to each well of a 96-well microtitre plate. The protein is allowed to coat overnight at 4° C. The plate is blocked with 150 µl of PBS-BSA (1% w/v) in each well for 1 hour at room temperature (RT) with mixing and then washed three times with 150 µl of PBST (0.05% v/v). Pig sera are diluted 1:800 in 100 µl of PBST-BSA (0.1% w/v) and incubated at RT for 2 hours with mixing. Plates are washed before adding 100 µl of goat anti-swine IgG (whole molecule)-HRP diluted 1:5,000 in PBST. After incubating for 1 hr at RT, the plates are washed and 100 µl of TMB substrate added. Colour development is allowed to occur for 10 minutes at RT before being stopped with the addition of 50 µl of 1 M sulphuric acid. The optical density of each well is read at 450 nm. Pooled serum from pigs of different sources and health status were used in this analysis. These included pigs from high health status herds (N1-N3), hyperimmunised pigs (M1-M3), experimentally challenged pigs (H1-H5) and recovered pigs from different herds (H6-H13).

As shown in Tables 5A and 5B, all proteins reacted strongly with serum from the pig hyperimmunised with *B. hyodysenteriae* bacteria (M1; 1.504310.1417) and reacted less strongly with serum from pigs hyperimmunised with *B. pilosicoli* (M2; 1.107510.1657) and *B. innocens* (M3; 1.121710.1584) indicating some level of cross-reactivity with pigs recognising other *Brachyspira* spp. The proteins reacted weakest with serum taken from high-health status pigs (N1-N3; 0.3008 to 0.4488), followed by experimentally challenged pigs showing acute severe symptoms of SD (H1-H5; 0.4514 to 0.9890), and strongest with pigs which had recovered from SD (H6-H13; 0.8039 to 1.0053). As a whole, these results indicate that all these OMP are immunogenic in naturally and experimentally infected pigs.

TABLE 5A

REACTIVITY OF TOXIN PROTEINS WITH HEALTHY PIG SERUM AND HYPERIMMUNISED PIG SERUM.

| | ELISA Reactivity (absorbance) | | | | | |
|---|---|---|---|---|---|---|
| Protein | N1 | N2 | N3 | M1 | M2 | M3 |
| H77 | 0.3875 | 0.4382 | 0.4391 | 1.5461 | 1.0049 | 1.1034 |
| H105 | 0.3286 | 0.4420 | 0.4478 | 1.4825 | 1.3311 | 1.1852 |
| H109 | 0.3102 | 0.3127 | 0.3813 | 1.4561 | 1.0572 | 1.1465 |
| H114 | 0.3786 | 0.3685 | 0.3789 | 1.4954 | 1.0146 | 1.0335 |
| H116 | 0.3712 | 0.4488 | 0.4003 | 1.5946 | 1.0794 | 0.9309 |
| H122 | 0.4407 | 0.3143 | 0.3369 | 1.4787 | 1.0216 | 1.1087 |
| H147 | 0.3516 | 0.3492 | 0.3279 | 1.5197 | 1.2794 | 1.2972 |
| H155 | 0.3008 | 0.3861 | 0.3764 | 1.4613 | 1.0717 | 1.1685 |

N1, N2, N3: pooled serum from high-health status pigs;
M1: serum from pig hyperimmunised with *B. hyodysenteriae* bacterin;
M2: serum from pig hyperimmunised with *B. pilosicoli* bacterin;
M3: serum from pig hyperimmunised with *B. innocens* bacterin.

TABLE 5B

REACTIVITY OF TOXIN PROTEINS WITH NATURALLY AND EXPERIMENTALLY INFECTED PIG SERUM.

| | ELISA Reactivity (absorbance) | | | | | | | | | | | | |
|---|---|---|---|---|---|---|---|---|---|---|---|---|---|
| Protein | H1 | H2 | H3 | H4 | H5 | H6 | H7 | H8 | H9 | H10 | H11 | H12 | H13 |
| H77 | 0.6616 | 0.6254 | 0.7151 | 0.7157 | 0.8161 | 0.883 | 0.9423 | 0.9849 | 0.8030 | 0.9857 | 0.9597 | 0.9944 | 0.8550 |
| H105 | 0.6664 | 0.7221 | 0.775 | 0.5747 | 0.8415 | 0.8097 | 0.9992 | 0.8891 | 0.8278 | 0.8657 | 0.8053 | 0.9145 | 0.8470 |
| H109 | 0.7616 | 0.7699 | 0.6373 | 0.6871 | 0.9687 | 0.8703 | 0.8235 | 0.8639 | 0.9431 | 0.8524 | 0.8612 | 0.9485 | 0.9471 |
| H114 | 0.7472 | 0.5604 | 0.7420 | 0.5513 | 0.9620 | 0.8422 | 0.9669 | 0.9947 | 0.9576 | 0.9885 | 0.9674 | 0.9999 | 0.8154 |
| H116 | 0.6574 | 0.5964 | 0.4580 | 0.5442 | 0.9314 | 0.9241 | 0.9110 | 0.8690 | 0.8039 | 0.8173 | 0.9652 | 0.9938 | 0.9128 |
| H122 | 0.5198 | 0.5043 | 0.5647 | 0.7717 | 0.8122 | 0.8955 | 0.8049 | 0.9258 | 0.9486 | 0.9854 | 0.8141 | 0.9292 | 0.9236 |
| H147 | 0.5795 | 0.6042 | 0.7623 | 0.4514 | 0.989 | 0.905 | 1.0002 | 0.8228 | 0.9975 | 0.8799 | 0.9884 | 1.0053 | 1.0031 |
| H155 | 0.6238 | 0.6096 | 0.6202 | 0.6937 | 0.9357 | 1.0025 | 0.8724 | 0.8837 | 0.8836 | 0.9419 | 0.8043 | 0.8777 | 0.9012 |

H1, H2, H3, H4, H5; pooled serum from experimentally infected pigs showing acute severe clinical signs of SD
H6, H7, H8, H9, H10, H11, H12, H13; pooled serum from commercial pigs recovered from SD Cloning of the various inserts into the pET-19b expression vector produced recombinant constructs of various sizes. Nucleotide sequencing of the pET-19b constructs verified that the expression cassette is in the correct frame for all the constructs. The predicted translation of the pET-19b expression cassette indicated that all the recombinant his-tagged proteins and the deduced amino acid sequence of the native spirochaete proteins were identical.

Example 24

Expression and Purification of Recombinant Proteins

Expression of the selected recombinant E. coli clones is performed in medium-scale to generate sufficient recombinant protein for vaccination of mice. All genes cloned produce recombinant proteins possessing the hexa-histidine fusion with an apparent molecular weight similar to the predicted molecular weight of the native protein as shown in Table 4. All recombinant proteins were highly reactive in western blotting using the anti-his antibody. Purification of the his-tagged recombinant proteins is by affinity chromatography under denaturing conditions. SDS-PAGE and Coomassie Blue staining of all recombinant proteins show purification of the proteins.

Example 25

Vaccination of Pigs Using the Purified Recombinant His-Tagged Proteins

Multiple purified recombinant his-tagged proteins (0.5 mg of each) were pooled in a total volume of 1 ml. Three vaccines were made:

(A) Recombinant vaccine 1 consisting of: NAV-H77, NAV-H105, NAV-H109 and NAV-H114;

(B) Recombinant vaccine 2 consisting of NAV-H116, NAV-H122, NAV-H147 and NAV-H155;

(C) Recombinant vaccine 3 consisting of NAV-H161 and NAV-H173.

Three groups of ten sero-negative pigs (5 weeks old) were injected intramuscularly with 2 ml of vaccine consisting of 2 mg of the pooled antigen emulsified with a water-in-oil adjuvant. The pigs were vaccinated twice intramuscularly into the back of the neck at 5 weeks of age and at 8 weeks of age. All pigs were bled immediately before the first vaccination, immediately before the second vaccination and two weeks after the second vaccination. Serum was collected from the blood and used to measure immune-responsiveness to the proteins contained in the vaccines. Since four proteins are combined in each vaccine, serum from each group of pigs is tested against all four proteins individually. The ELISA was performed the same way as outlined in Example 22.

As shown in Table 6, all pigs responded strongly to the vaccination regime given with antibody levels increasing significantly after the first (9.08-fold-16.53-fold increase; $P<0.001$) and second (2.27-fold-2.59-fold increase; $P<0.001$) intramuscular injections. These results clearly demonstrate the immunogenicity of these OMP proteins in pigs and the effectiveness of the vaccination regime in inducing high antibody levels in the pig.

TABLE 6

IMMUNOGENICITY OF TOXIN PROTEINS IN PIGS FOLLOWING INTRAMUSCULAR VACCINATION. ALL ELISA VALUES ARE EXPRESSED AS MEAN ABSORBANCE ± STANDARD DEVIATION

| | Pre-Vacc. | Pre-Boost | | Post-vaccination (2 weeks) | |
|---|---|---|---|---|---|
| Protein | ELISA value | ELISA Value | Fold increase | ELISA value | Fold increase |
| H77 | 0.0671 ± 0.0295 | 1.1087 ± 0.2037 | 16.53 | 2.7387 ± 0.2990 | 2.47 |
| H105 | 0.0663 ± 0.0257 | 1.0746 ± 0.2087 | 16.20 | 2.6299 ± 0.2854 | 2.45 |
| H109 | 0.0822 ± 0.0235 | 1.0443 ± 0.1932 | 12.70 | 2.7071 ± 0.2785 | 2.59 |
| H114 | 0.0661 ± 0.0280 | 1.0480 ± 0.2105 | 15.85 | 2.5951 ± 0.2955 | 2.48 |
| H116 | 0.1096 ± 0.0244 | 0.9952 ± 0.1455 | 9.08 | 2.2555 ± 0.2482 | 2.27 |
| H122 | 0.0904 ± 0.0327 | 1.0498 ± 0.2686 | 11.62 | 2.6590 ± 0.2354 | 2.53 |
| H147 | 0.0682 ± 0.0354 | 1.0654 ± 0.1386 | 15.63 | 2.6027 ± 0.2085 | 2.44 |
| H155 | 0.0831 ± 0.0298 | 1.0407 ± 0.2497 | 12.52 | 2.6112 ± 0.3649 | 2.51 |

Example 26

Protection of Pigs by Vaccination with Purified Recombinant His-Tagged Proteins Multiple purified recombinant his-tagged proteins (0.5 mg of each) are pooled in a total volume of 1 ml. Three vaccines are made:

a) Recombinant vaccine 1 consisting of: NAV-H77, NAV-H105, NAV-H109 and NAV-H114;

b) Recombinant vaccine 2 consisting of: NAV-H116, NAV-H122, NAV-H147 and NAV-H155;

c) Recombinant vaccine 3 consisting of NAV-H161 and NAV-H173.

Four groups of ten sero-negative pigs (5 weeks old) are injected intramuscularly with 2 ml of vaccine consisting of 2 mg of the pooled antigen emulsified with a water-in-oil adjuvant. A fifth group of ten sero-negative pigs is used as negative controls and are sham vaccinated with PBS emulsified in the adjuvant. All the pigs are vaccinated twice intramuscularly into the back of the neck at 5 weeks of age and at 8 weeks of age. All pigs are challenged with 100 ml of an active *B hyodysenteriae* culture (~$10^9$ cells/ml) by gastric gavage at ten weeks of age, and pigs are observed daily for clinical signs of swine dysentery during the experiment (up to six weeks post-challenge) and at post-mortem examination. Twice weekly, all pigs are rectally swabbed for selective bacteriological culture.

The invention claimed is:

1. An isolated polynucleotide that encodes a polypeptide comprising the amino acid sequence of SEQ ID NO: 8.

2. The isolated polynucleotide of claim 1, wherein the isolated polynucleotide comprises the nucleotide sequence of SEQ ID NO: 7.

3. A plasmid comprising the polynucleotide of claim 1.

4. The plasmid of claim 3, wherein said plasmid is an expression vector.

5. A cell containing the plasmid of claim 3.

6. An isolated protein comprising the amino acid sequence of SEQ ID NO: 8.

7. An immunogenic composition comprising:
(a) a plasmid comprising a polynucleotide that encodes the amino acid sequence of SEQ ID NO:8,
(b) a cell containing the plasmid comprising a polynucleotide that encodes the amino acid sequence of SEQ ID NO:8, or
(c) an isolated protein comprising the amino acid sequence of SEQ ID NO: 8.

8. A method of diagnosing *Brachyspira* infection comprising:
(a) providing a sample from an animal suspected of being infected with *Brachyspira;*
(b) contacting the sample with one or more isolated polypeptides comprising an amino acid sequence of SEQ ID NO: 8;
(c) incubating the sample and polypeptide under conditions which allow for the formation of antibody-antigen complexes; and
(d) determining whether an antibody-antigen complex with one or more polypeptides is formed, wherein the formation of an antibody-antigen complex indicates the animal is infected with *Brachyspira.*

9. The method of claim 8, wherein the *Brachyspira* infection is infection with *Brachyspira hyodysenteriae.*

10. A kit for diagnosing *Brachyspira* infection comprising one or more isolated polypeptides comprising an amino acid sequence of SEQ ID NO: 8.

\* \* \* \* \*